(12) United States Patent
Pan et al.

(10) Patent No.: US 9,395,313 B2
(45) Date of Patent: Jul. 19, 2016

(54) ADVANCED COLLIMATOR APERTURE CURVE

(71) Applicant: GE MEDICAL SYSTEMS GLOBAL TECHNOLOGY COMPANY, LLC, Waukesha, WI (US)

(72) Inventors: Xianjun Pan, Beijing (CN); Shutao Liu, Chengdu (CN); Dong Zhang, Chengdu (CN); Bin Wang, ChengDu (CN)

(73) Assignee: GE MEDICAL SYSTEMS GLOBAL TECHNOLOGY COMPANY, LLC, Waukesha, WI (US)

( * ) Notice: Subject to any disclaimer, the term of this patent is extended or adjusted under 35 U.S.C. 154(b) by 185 days.

(21) Appl. No.: 14/168,100

(22) Filed: Jan. 30, 2014

(65) Prior Publication Data

US 2014/0211913 A1    Jul. 31, 2014

(30) Foreign Application Priority Data

Jan. 31, 2013 (CN) .......................... 2013 1 0037469

(51) Int. Cl.
| | |
|---|---|
| *G01N 23/04* | (2006.01) |
| *A61B 6/03* | (2006.01) |
| *A61B 6/06* | (2006.01) |
| *G21K 1/02* | (2006.01) |

(52) U.S. Cl.
CPC .............. *G01N 23/046* (2013.01); *A61B 6/032* (2013.01); *A61B 6/06* (2013.01); *G01N 2223/419* (2013.01); *G21K 1/02* (2013.01)

(58) Field of Classification Search
CPC ............ A61B 6/03; A61B 6/032; A61B 6/06; A61B 6/035; A61B 6/4078; G21K 1/02; G21K 1/025; G21K 1/04; G01N 23/046
USPC ........................................ 378/4, 16, 147–153
See application file for complete search history.

(56) References Cited

U.S. PATENT DOCUMENTS

| | | | | |
|---|---|---|---|---|
| 5,644,614 | A * | 7/1997 | Toth ...................... | A61B 6/032 378/145 |
| 6,396,902 | B2 | 5/2002 | Tybinkowski et al. | |
| 7,317,786 | B2 * | 1/2008 | Distler .................... | A61B 6/06 378/145 |
| 7,852,990 | B2 * | 12/2010 | Aulbach ................. | A61B 6/06 378/148 |
| 2002/0015474 | A1 * | 2/2002 | Tybinkowski .......... | G21K 1/025 378/153 |
| 2003/0099323 | A1 * | 5/2003 | Nagata et al. .................... | 378/4 |
| 2011/0211667 | A1 * | 9/2011 | Ikhlef et al. .................... | 378/19 |

* cited by examiner

*Primary Examiner* — Robert Kim
*Assistant Examiner* — David E Smith
(74) *Attorney, Agent, or Firm* — GE Global Patent Operation

(57) ABSTRACT

A CT imaging system and a method for determining a CT collimator slit profile. The method includes determining a profile of two opposite edges of the collimator slit in a longitudinal direction thereof based on the following: a vertical distance between a focus of a radiation source to the collimator slit, a vertical distance between the focus and the radiation detector, an inclination angle between adjacent detector elements, a length of each detector element, a desired width of projection on the radiation detector by the radiation rays passing through the slit whose longitudinal edge profile is to be determined, and an offset angle of a connecting line from a point on a longitudinal center line of the slit to the focus relative to a plane passing said focus and perpendicular to the slit.

14 Claims, 13 Drawing Sheets

ADVANCED COLLIMATOR APERTURE CURVE

TECHNICAL FIELD

Embodiments of the present invention relate to the field of radiation CT and, more specifically, to a method for determining a CT collimator slit profile and a CT imaging system that can avoid additional radiation dose while maintaining detection accuracy.

BACKGROUND ART

At present, radiation CT systems such as X-ray CT systems are widely used in various medical institutions for three-dimensional imaging of the regions of interest of the subjects to assist the clinicians to achieve an accurate medical diagnosis of the subjects.

In a radiation CT system, a radiation tube generating cone-shaped radiation beams and a two-dimensional radiation area detector detecting the radiation are placed in rotation around a rotation center, wherein the two-dimensional radiation area detector is disposed opposite to the radiation tube and consists of detector elements arranged in a matrix. Projection data generated by the radiation rays transmitting through the subject are collected; based on the collected projection data, an image of the region of interest of the subject is reconstructed; and then the reconstructed CT image is displayed on an image display device.

In a radiation CT system, a collimator is generally provided between the radiation tube and the subject to be detected. By adjusting the slit width of the collimator, the width of the radiation beam in a direction parallel to the subject is controlled so as to control the thickness of the scan.

In one conventional type of collimator, the longitudinal edges of the slit thereof have a linear shape. Because the rectangular X-ray detector is usually placed in an arc surface centered on the focus of the X-ray tube, the X-ray beam projected onto the X-ray detector by using such a conventional collimator forms a projection range that has an irregular rectangular shape, thus reducing the detection accuracy and resulting in an additional dose of radiation to the subject.

Another conventional type of collimator and its slit are configured to have a curved shape, so that the arc surface where the collimator is located and the arc surface where the rectangular X-ray detector is located are both centered on the focus of the X-ray tube. Accordingly, the X-ray beam projected onto the X-ray detector by using such a conventional collimator forms a projection range that has a regular rectangular shape. However, due to limitations on the materials of the collimator, it is difficult to produce a collimator having a curved shape and the processing difficulty and cost involved are high.

At present, there is a further, plate type collimator in which the slit profile is designed by using a general formula for a CT collimator slit profile. Such a collimator can enable the X-ray beam projected onto the X-ray detector consisting of rectangular units to form a projection that is close to the profile of the X-ray detector itself, but it is still defective in that a large number of over-shoot and short-shoot areas exist.

Therefore, there is a need for a method capable of quickly and easily determining the CT collimator slit profile and a CT imaging system capable of avoiding additional radiation dose while maintaining detection accuracy.

SUMMARY OF THE INVENTION

The present invention provides a method for determining a CT collimator slit profile and a CT imaging system that can solve the above problems.

According to a first aspect of the present invention, there is provided a radiation CT imaging system comprising: a radiation source arranged on a scan gantry and at the side of a subject to be examined for emitting radiation rays to the subject; a collimator disposed between the subject and the radiation source for beamforming the radiation rays from said radiation source before projecting them to the subject; a radiation detector disposed on the scan gantry and at the other side of the subject for detecting the radiation rays transmitted through the subject; wherein said radiation detector comprises a plurality of detector elements arranged in a row, and there is an inclination angle between adjacent detector elements, wherein the collimator comprises a planar gating device, which is provided with one or more slits for passage of the radiation rays, and wherein the width distribution of each slit in the longitudinal direction of the collimator is determined jointly by the following: the vertical distance between the focus of the radiation source and said slit, the vertical distance between the focus and the radiation detector, the inclination angle between adjacent detector elements, the length of each detector element, the desired width of projection on the radiation detector by the radiation rays passing through the slit, and the offset angle of the connecting lines from a point on the longitudinal center line of the slit to the focus relative to a plane passing said focus and perpendicular to the slit.

In the radiation CT imaging system according to the first aspect of the present invention, the radiation rays are X-rays.

The radiation CT imaging system according to the first aspect of the present invention, further comprises: a collimator controller configured to select from a plurality of slits one slit by which the width of the projection of the radiation rays on the radiation detector meets the examination requirements of the subject.

In the radiation CT imaging system according to the first aspect of the present invention, the plurality of detector elements may have same or different length.

In the radiation CT imaging system according to the first aspect of the present invention, the inclination angles between all adjacent detector elements are equal.

In the radiation CT imaging system according to the first aspect of the present invention, at least two inclination angles of the inclination angles between all adjacent detector elements are not equal.

In the radiation CT imaging system according to the first aspect of the present invention, the plurality of detector elements includes 3 to 7 detector elements.

According to a second aspect of the present invention, there is provided a method for determining a slit profile of a CT collimator, wherein said CT collimator comprises a planar structure gating device on which one or more slits are arranged to allow radiation rays from a radiation source to be used in cooperation with the CT collimator to pass through and then projected, after passing through a subject to be examined, to a radiation detector to be used in cooperation with the CT collimator, wherein said radiation detector comprises a plurality of detector elements arranged in a row and there is an inclination angle between two adjacent detector elements. The method for determining the slit profile of a CT comprises: determining each slit of the one or more slits the profile of the two opposite edges in the longitudinal direction thereof based on the following: the vertical distance between the focus of the radiation source to the slit, the vertical distance between the focus and the radiation detector, the inclination angle between the adjacent detector elements, the length of each detector element, the desired width of projection on the radiation detector by the radiation rays passing through the slit, and the offset angle of a connecting line from a point on a longitudinal center line of the slit to the focus relative to a plane passing said focus and perpendicular to the slit.

In the method according to the second aspect of the present invention, the radiation rays are X-rays.

In the method according to the second aspect of the present invention, the plurality of detector elements may have the same or different length.

In the method according to the second aspect of the present invention, the inclination angles between all adjacent detector elements are equal.

In the method according to the second aspect of the present invention, at least two inclination angles of the inclination angles between all adjacent detector elements are not equal.

In the method according to the second aspect of the present invention, the plurality of detector elements includes 3 to 7 detector elements.

The determination of the slit edge profile of the collimator according to the present invention takes into account not only the positional relationship between the collimator, the radiation detector and the radiation source, but also the structural and positional relationship between the individual detector elements in the radiation detector. Therefore, without consideration of the apparatus installation deviation, the use of the collimator according to the present invention can enable the actual projection distribution of the radiation beam projected on the radiation detector through the collimator to be fully equal to the ideal projection distribution, thereby avoiding or reducing the additional radiation dose while maintaining detection accuracy.

In the following specification and claims, the singular forms "a", "an" and "the" include plural referents, unless the context clearly dictates otherwise. Moreover, the suffix "(s)" as used herein is usually intended to include both the singular and the plural of the term that it modifies, thereby including one or more of that term. The terms "first," "second," and the like, herein do not denote any order, quantity, or importance, but rather are used to distinguish one element from another or one embodiment from another.

Reference throughout the specification to "one embodiment," "another embodiment," "an embodiment," "some embodiments," and so forth, means that a particular element (e.g., feature, structure, and/or characteristic) described in connection with the invention is included in at least one embodiment described herein, and may or may not be present in other embodiments. In addition, it is to be understood that the described inventive features may be combined in any suitable manner in the various embodiments and configurations.

Embodiments of the present disclosure will be described hereinbelow with reference to the accompanying drawings. In the following description, well-known functions or constructions are not described in detail to avoid obscuring the disclosure in unnecessary detail.

BRIEF DESCRIPTION OF THE DRAWINGS

In the following, some exemplary embodiments of the present invention will be described in detail with reference to the drawings, wherein like or similar elements are denoted by the same reference numerals and wherein.

DETAILED DESCRIPTION

In the following some exemplary embodiments of the present invention will be described with reference to the drawings. However, it will be appreciated by persons skilled in the art that the present invention is not limited to these exemplary embodiments.

Figure 1A:
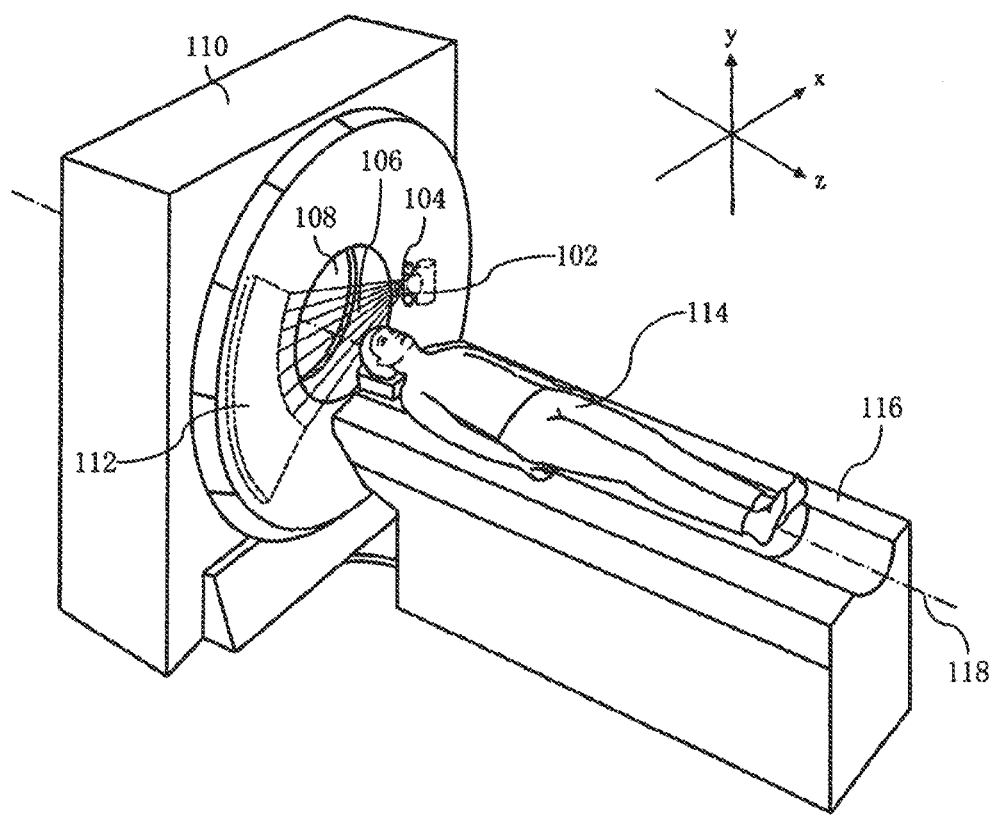
FIGS. 1A and 1B show a radiation CT system according to an exemplary embodiment of the present invention.
Figure 1B:
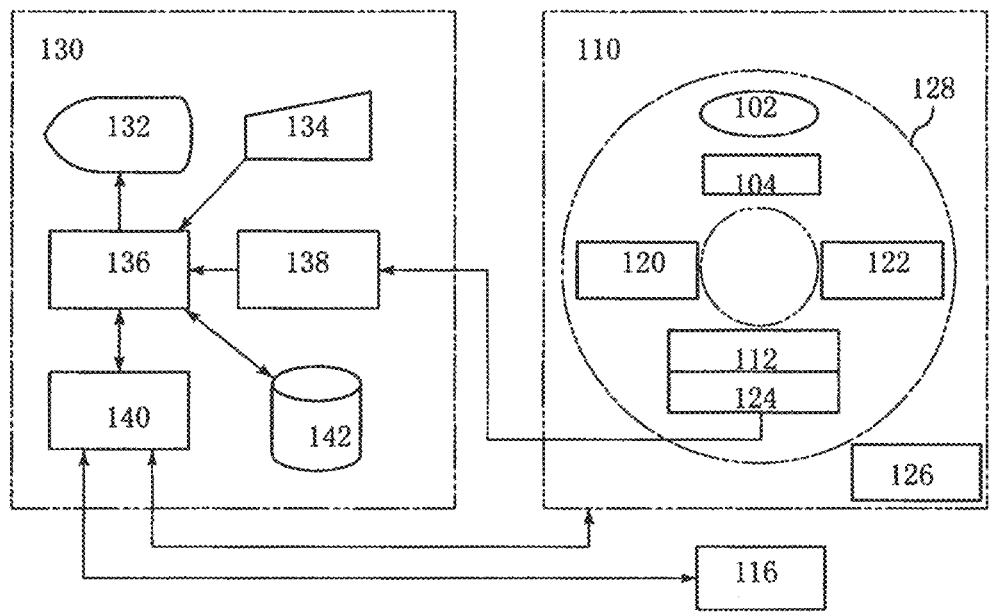

FIGS. 1A and 1B show a radiation CT system 100 according to an exemplary embodiment of the present invention. In one embodiment, the radiation CT system 100 is an X-ray CT system.

As shown in FIGS. 1A-1B, the X-ray CT system 100 mainly includes three parts: a scan gantry 110, a support table 116 for supporting and positioning a subject 114 to be detected, and an operation console 130. The scan gantry 110 includes an X-ray tube 102. X-rays 106 emitted from the X-ray tube 102 pass through a collimator 104 to form an X-ray beam of such shapes as a fan shaped beam and a cone shaped beam, to be irradiated to a region of interest of the subject 114. The X-ray beam that passes through the region of interest of the subject 114 is applied to an X-ray detector 112 disposed on the other side of the subject 114. The X-ray detector 112 has a plurality of two-dimensional X-ray detecting units in the propagation direction (the signal channel direction) and the thickness Z direction (column direction) of the fan-shaped X-ray beam. Optionally, a collimator component (not shown in FIGS. 1A and 1B) is arranged between the X-ray detector 112 and the subject 114 to be examined, to calibrate the X-ray beam passing through the subject 114 before it impinges on the X-ray detector 112.

A data acquisition system (DAS) 124 is coupled to the X-ray detector 112. The data acquisition system 124 collects the data detected by each of the X-ray detecting units of the X-ray detector 124 for use as the projection data. The X-ray radiation from the X-ray tube 102 is controlled by an X-ray controller 122. In FIG. 1B, the connections between the X-ray tube 102 and the X-ray controller 122 are not shown.

The data acquisition system 124 collects data related to the tube voltage and tube current applied to the X-ray tube 102 by the X-ray controller 122. In FIG. 1B, the connections between the X-ray controller 122 and the data acquisition system 124 are omitted.

The collimator 104 is controlled by a collimator controller 120. In one embodiment, the collimator 104 and the collimator controller 120 are two separate components. In another embodiment, the collimator controller 120 may be disposed within the collimator 104. In FIG. 1B, the connections between the collimator 104 and the collimator controller 120 are omitted.

Components like the X-ray tube 102, the collimator 104, the X-ray detector 112, the data acquisition system 124, the X-ray controller 122 and the collimator controller 120 are mounted in a rotating portion 128 of the scan gantry 110. The rotating portion 128 rotates under the control of a rotation controller 126. In FIG. 1B, the connections between the rotating portion 128 and the rotation controller 126 are not shown.

Under the action of a drive system such as a motor, the support table 116 can be moved together with the subject 114 carried thereon along a longitudinal axis 118 of the subject into an opening 108 of the scan gantry 110, so that the region of interest of the subject 114 is substantially perpendicular to the X-ray beam irradiated thereon through the collimator 104.

The operation console 130 has a central processor 136 such as a computer. A control interface 140 is connected to the central processor 136. The scan gantry 110 and the support table 116 are connected to the control interface 140. The central processor 136 controls the scan gantry 110 and the support table 116 through the control interface 140.

The data acquisition system 124, the X-ray controller 122, the collimator controller 120 and the rotation controller 126 in the scan gantry 110 are controlled through the control interface 140. In FIG. 1B, the separate connections between the relevant parts and the control interface 140 are not shown.

A data acquisition buffer 138 is connected to the central processor 136. The data acquisition system 124 of the scan gantry 110 is connected to the data acquisition buffer 138. Projection data collected by the data acquisition system 124 are inputted to the central processor 136 through the data acquisition buffer 138.

The central processor 136 uses the projection data inputted from the data acquisition buffer 138 to perform an image reconstruction. In performing image reconstruction, such methods as the filtered back projection method, and three-dimensional image reconstruction method can be used. A storage device 142 is connected to the central processor 136. The storage device 142 may be used to store data, reconstructed images and procedures for implementing the various functions of the X-ray CT system 100.

A display device 132 and an input device 134 are connected to the central processor 136, respectively. The display device 132 displays the reconstructed images and other information output from the central processor 136. An operator can input various instructions and parameters to the central processor 136 through the input device 134. Through the display device 132 and the input device 134, the operator can achieve an interactive operation of the X-ray CT system 100.

Figure 2:
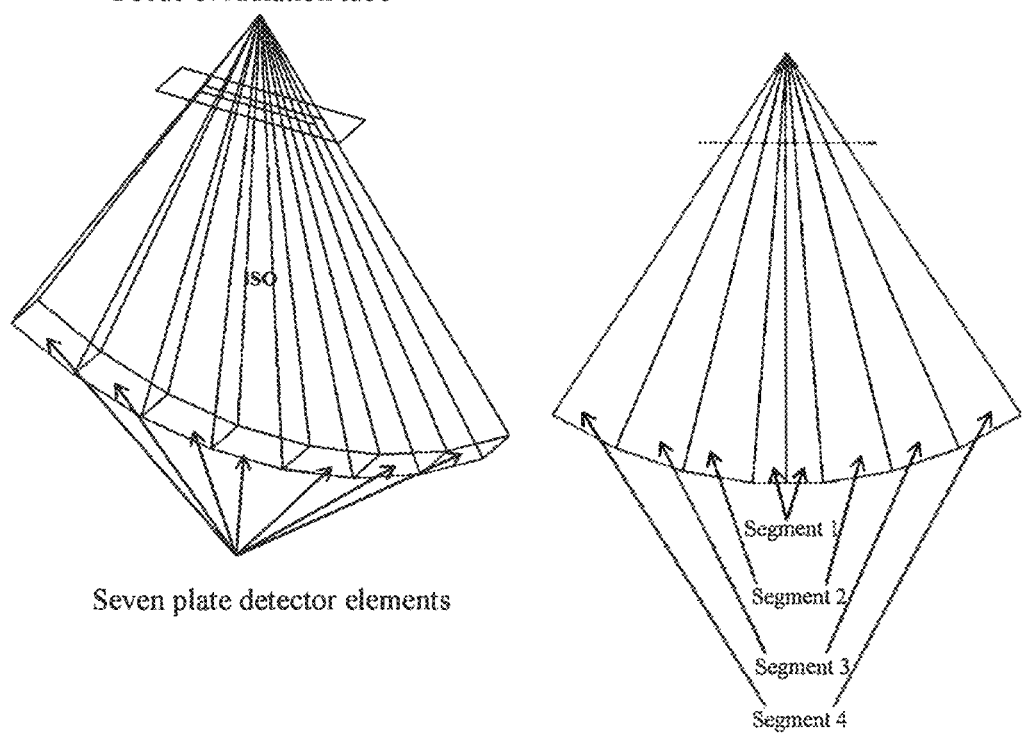
FIG. 2 shows an arrangement of a radiation detector according to an exemplary embodiment of the present invention.
Figure 3:
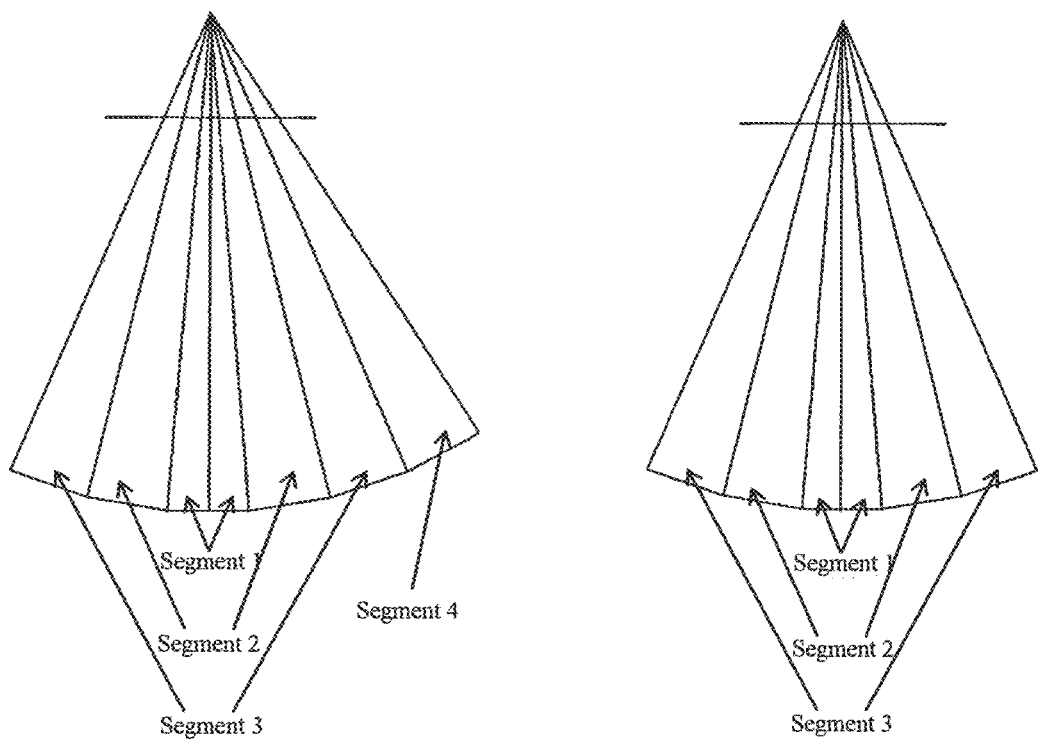
FIG. 3 shows an arrangement of a radiation detector according to two other exemplary embodiments of the present invention.
Figure 4:
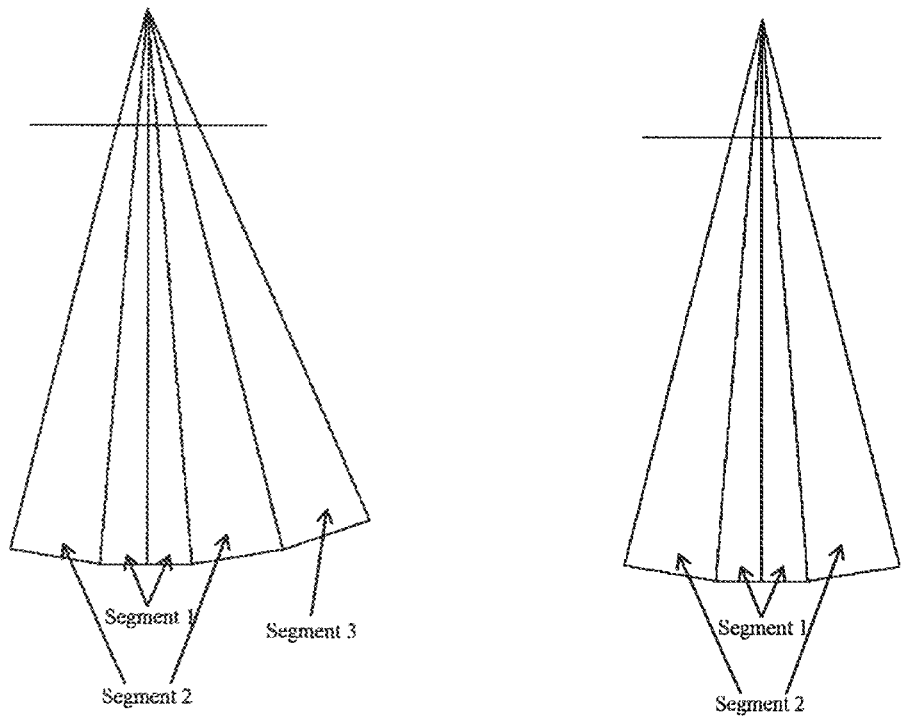
FIG. 4 shows an arrangement of a radiation detector according to another two exemplary embodiments of the present invention.

FIG. 2 illustrates a radiation detector according to an exemplary embodiment of the present invention. As shown in FIG. 2, the X-ray detector 112 includes a plurality of plate detector elements arranged in a row. More particularly, the plurality of plate detector elements may include 3 to 7 detector elements. FIG. 3 shows a radiation detector according to two other exemplary embodiments of the present invention. As shown in the left part of FIG. 3, the X-ray detector 112 includes six plate detector elements arranged in a row. As shown in the right part of FIG. 3, the X-ray detector 112 includes five plate detector elements arranged in a row. FIG. 4 shows a radiation detector according to another two exemplary embodiments of the invention. As shown in the left part of FIG. 4, the X-ray detector 112 comprises four plate detector elements arranged in a row. As shown in the right part of FIG. 4, the X-ray detector 112 comprises three plate detector elements arranged in a row.

Adjacent detector elements in the plurality of plate detector elements constituting the X-ray detector 112 have the same or different inclination angles, as shown in FIGS. 2-4. The plurality of plate detector elements may have the same or different length, and may have the same or different width. For simplicity, the detector elements shown in FIGS. 2-4 have the same width and the same length, and the inclination angles between any two adjacent detector elements are the same.

Figure 5A:
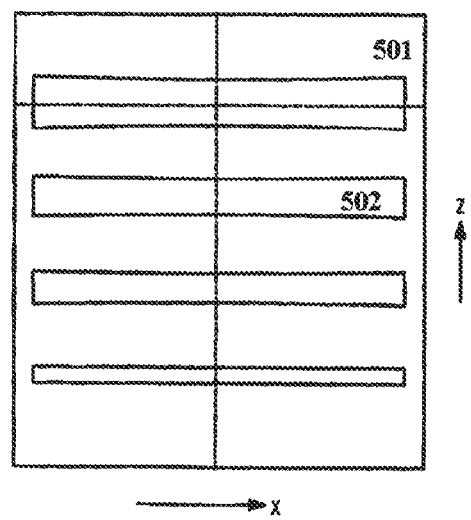
FIGS. 5A and 5B show a structure of a collimator gating device according to an exemplary embodiment of the present invention.
Figure 5B:
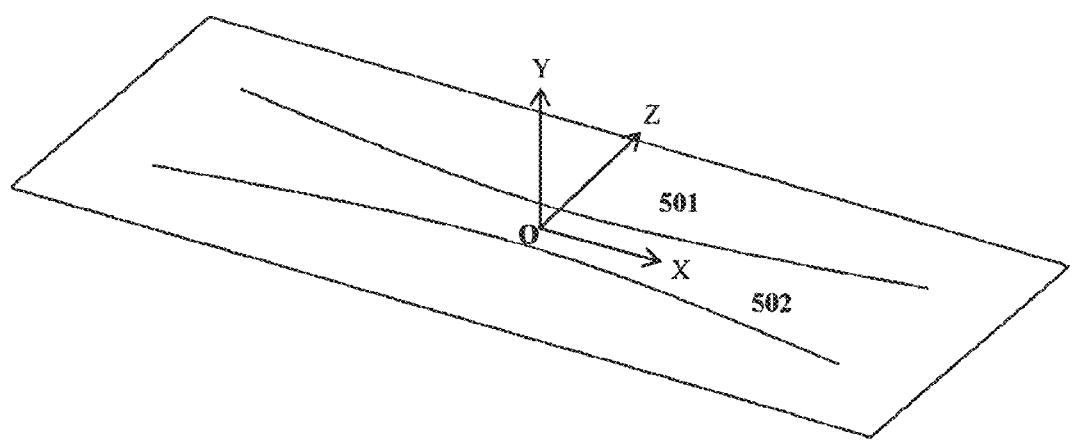

FIGS. 5A and 5B illustrate a collimator gating device 501 of a collimator 104 according to an exemplary embodiment of the present invention. As shown in FIG. 5A, the collimator 104 has a planar structure and includes a gating device 501 for blocking the passage of X-rays. The gating device 501 is provided with one or more slits 502 for passage of X-rays. The plurality of slits is aligned in parallel in the longitudinal direction of the slit and has different average widths to meet different detection requirements. Under the action of a drive unit (not shown), the gating device 501 can move to and fro along the Z direction shown in the figure, so that the collimator controller 120 can select a corresponding slit 502 to implement detection according to the detection needs of the subject.

FIG. 5B shows one slit 502 of the collimator 104. As shown in FIG. 5, a three-dimensional coordinate system XYZ may be established at the center O of the slit 502, wherein the connecting line from the focus F of the X-ray tube 102 to the center O of the slit is perpendicular to the plane of the collimator (the XOZ plane as shown in the Figure). The profile of the two opposite edges of the slit 502 along the slit longitudinal direction is related to the positional relationship between the X-ray tube 102, the collimator 104 and the X-ray detector 112, the desired width of projection on the X-ray detector 112 by the X-rays passing through the slit, and the structure of the X-ray detector 112.

For simplicity, the following the case, where the X-ray detector 112 comprises five identical detector elements arranged in a row and the inclination angles between any two adjacent detector elements are equal, is taken as an example to illustrate the relationship between the profile of the edges of the collimator slit 502 along the slit longitudinal direction and the positional relationship between the X-ray tube 102, the collimator 104 and the X-ray detector 112, the desired width of projection on the X-ray detector 112 by the X-rays passing through the slit 502, and the structure of the X-ray detector 112, wherein the inclination angle between adjacent detector elements is α.

Figure 6:
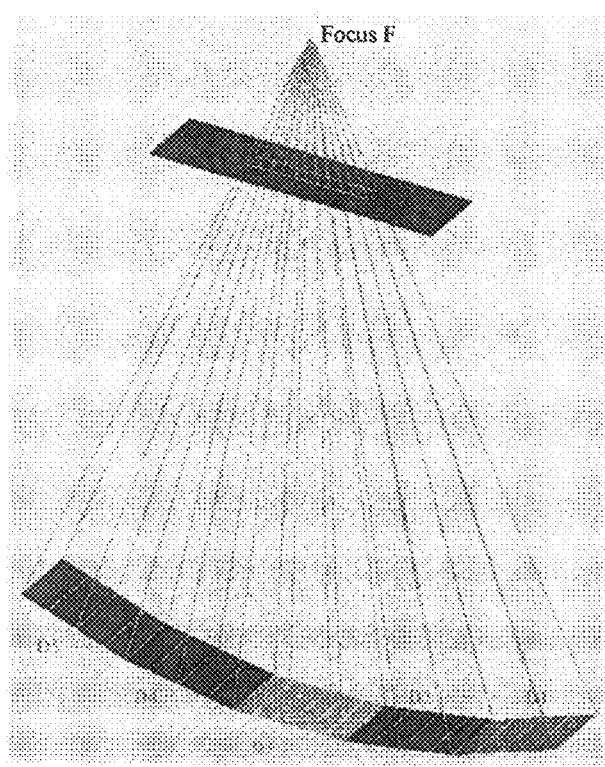
FIGS. 6 and 7 illustrate a layout between a radiation detector, a radiation tube, and a collimator according to an exemplary embodiment of the present invention.
Figure 7:
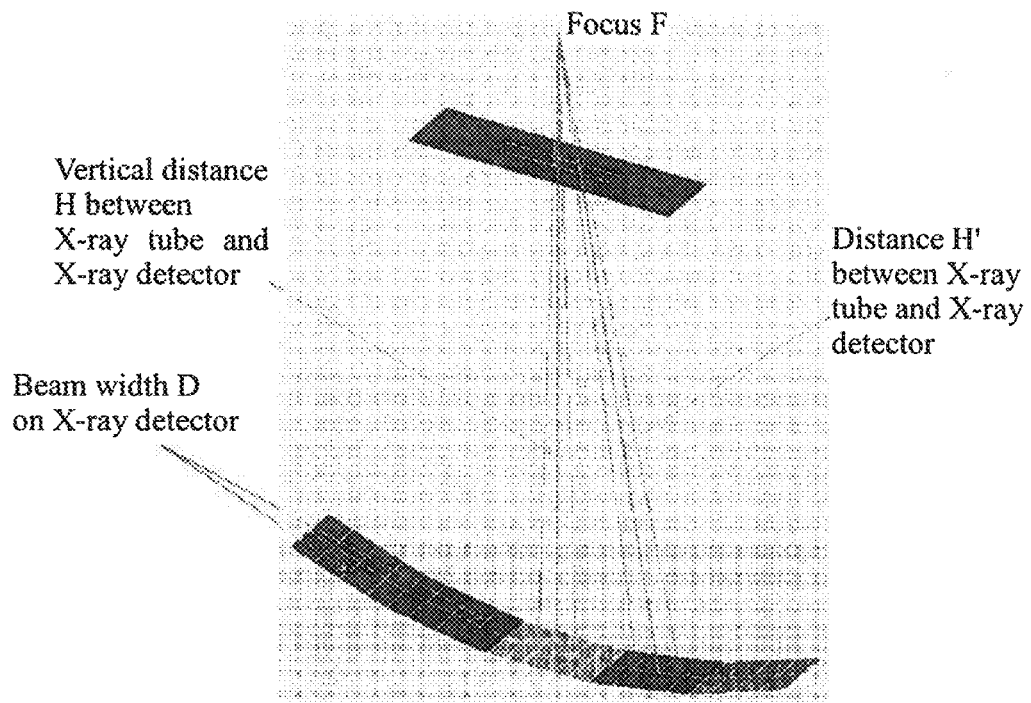

FIGS. 6 and 7 show the positional relationship between the X-ray detector 112 comprising five plate detector elements D1-D5, the focus F of the X-ray tube 102, and the collimator 104. As shown in FIGS. 6 and 7, the profile of the longitudinal edges of the slit 502 is such that X-rays passing through the slit form a rectangular projection area on the X-ray detector 112. The rectangular projection on the X-ray detector 112 by the X-rays passing through the slit of the plurality of slits having the largest average width has a width along the OZ axis that is equal to or less than the width of the X-ray detector along the OZ axis, and the rectangular projection on the X-ray detector 112 by the X-rays passing through the slit of the plurality of slits having the largest length has a length along the OX axis that is equal to or less than the total length L of the plurality of detector elements along the OX axis. As shown in FIG. 7, a straight line passing the focus F of the X-ray tube and the center O of the collimator slit is perpendicular to the detector element D3 in the middle of the X-ray detector 112, so that the vertical distance from the focus F of the X-ray tube to the X-ray detector 112 is H, and the distance from the focus F of the X-ray tube to the center of the second detector element D2 of the X-ray detector 112 is H'.

Figure 8:
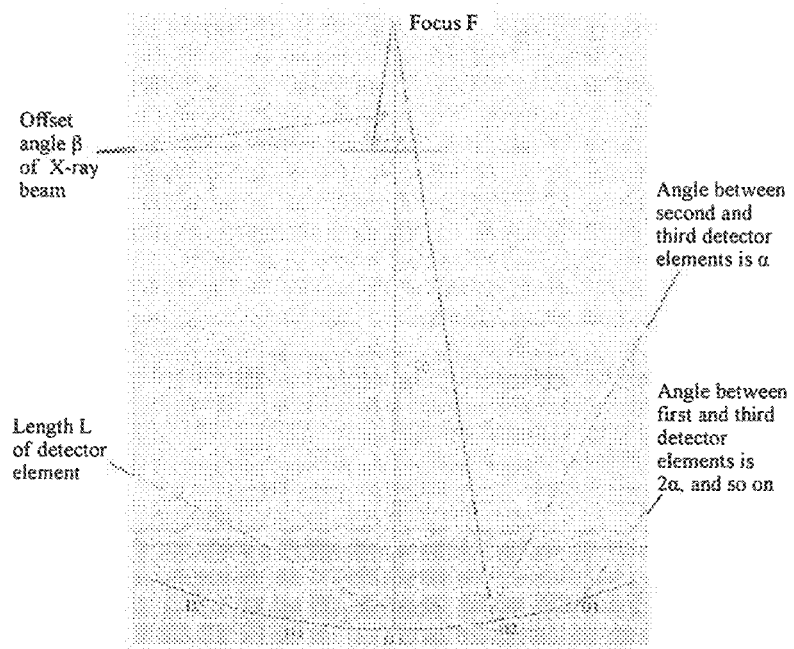
FIGS. 8, 9, 10, 11, 12, 13, 14, 15, 16, 17, 18, 19, and 20 illustrate a relationship between the structure of the radiation detector and the distribution of the two longitudinal edges of a single slit of the collimator according to an exemplary embodiment of the present invention.

As shown in FIG. 8, the X-ray beam projected onto the center of the detector element D2 through the selected collimator slit 502 from the X-ray tube 102 has an offset angle β relative to the vertical distance from the focus F of the X-ray tube 102 to the X-ray detector 112 (i.e., the liner distance between the focus F of the X-ray tube 102 and the center of the detector element D3), wherein each detector element has a length L and the projection formed on the X-ray detector 112 by the X-rays passing through the selected collimator slit 502 has a width D. Because the inclination angle between any two adjacent detector elements of the five detector elements is α, the inclination angle of the detector element D2 relative to the plane of the detector element D3 is α, the inclination angle of the detector element D1 relative to the plane of the detector element D3 is 2α, the inclination angle of a further detector element (if any) adjacent to the detector element D1 relative to the plane of the detector element D3 is 3α, and so on.

Figure 9:
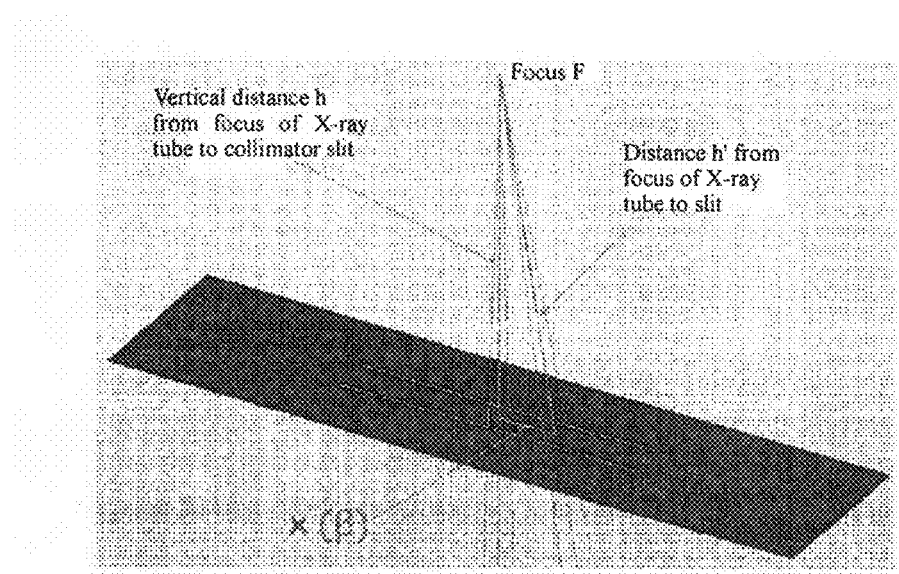

As shown in FIG. 9, the vertical distance from the focus F of the X-ray tube to the collimator slit 502, namely, the distance from the focus F of the X-ray tube to the center O of the collimator slit, is h. The coordinate of the X-ray beam having the offset angle β emitted from the focus F of the X-ray tube on the OX axis of the slit plane is X (β), and a distance from the focus F of the X-ray tube to the slit along the straight line of the X-ray beam having the offset angle β is h', said h' having the following relationship with the vertical distance h: h'=h/cos(β). Therefore, the following equation can be obtained:

$$x(\beta) = \pm \tan(\beta) \times h \quad (1),$$

wherein when the offset angle β of the X-ray beam is counterclockwise, equation (1) is a positive value; and when the offset angle β of the X-ray beam is clockwise, equation (1) is a negative value.

Figure 10:
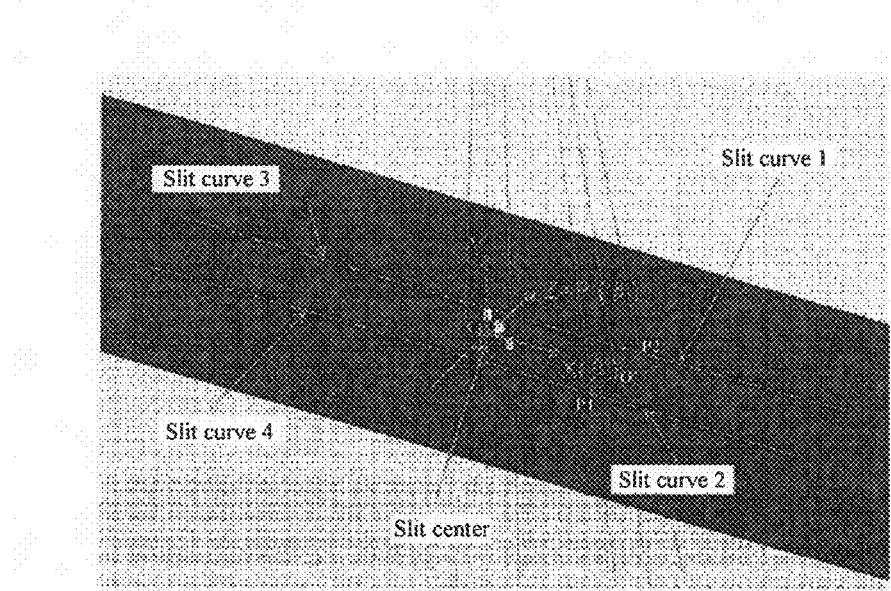

As shown in FIG. 10, given a three-dimensional coordinate system XYZ established at the center O of the collimator slit, then the X-ray beam passing between the longitudinal edges of the collimator slit will have a coordinate (x, z) in the collimator plane XOZ. The intersection O' between the X-ray beam having the offset angle β and the two-dimensional plane XOZ will have a coordinate (X(β), 0). Therefore, a straight line passing the intersection O' and parallel to the axis OZ will have two the intersection points P1 and P2, whose coordinates are (X(β), +z) and (X(β), −z) respectively, with the two longitudinal edges of the slit. Because the intersection points P1 and P2 on the longitudinal edges of the slit are symmetrically distributed relative to the axis OX, namely, the slit curves 1 and 2 corresponding to one detector element are symmetrically distributed relative to the axis OX, and the slit curves 3 and 4 corresponding to another detector element are symmetrically distributed relative to the axis OX. Thus, the coordinates of the intersection points P1 and P2 on the longitudinal edges of the slit can be uniformly represented as (X(β), P(β)), wherein the parameter P(β) may represent the profile distribution of the longitudinal edges of the slit in the two-dimensional plane XOZ.

Figure 11:
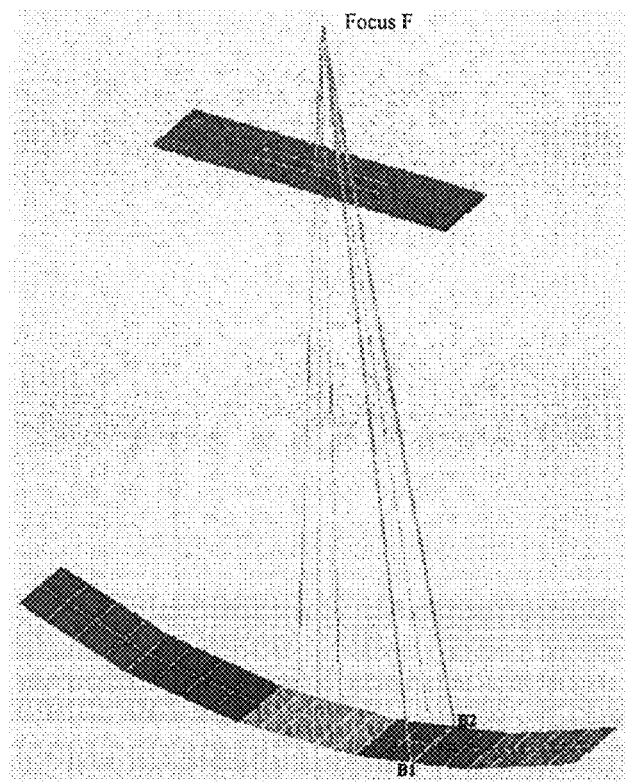

FIG. 11 shows the positional relationship between the plane of the X-ray beam having the offset angle β projected to the X-ray detector 112 and the vertical plane of the X-ray beam having an offset angle of 0. Since only X-rays between the edges of the slit can be projected onto the X-ray detector 112, the X-ray beam having the offset angle β forms an X-ray triangle, namely, ΔFB1B2. When the X-ray triangle ΔFB1B2 obtained in FIG. 11 is rotated counterclockwise an angle β taking the focus F of the X-ray tube as the rotation axis, a plurality of X-ray triangles as shown in FIG. 12 will be obtained.

Figure 12:
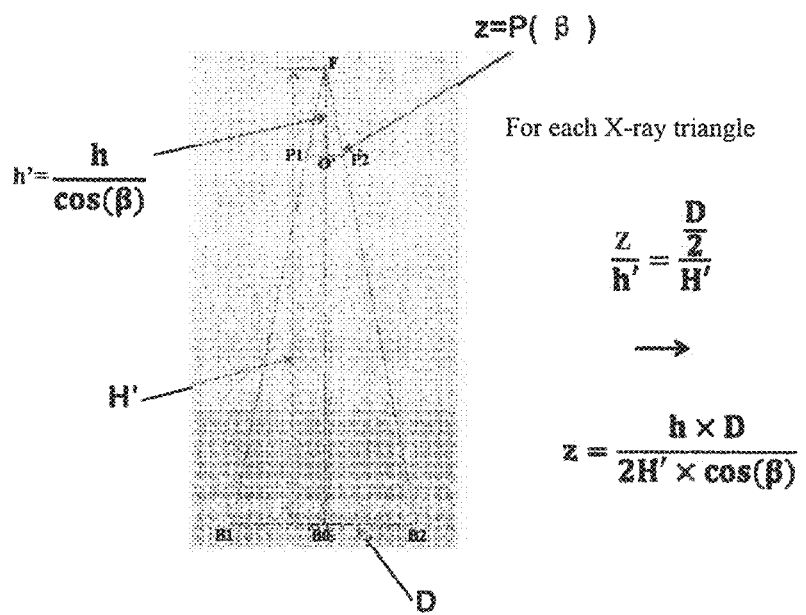

As shown in FIG. 12, the X-ray triangle ΔFO'P2 satisfies the following condition: O'F=h' and O'P2=z=P(β); the X-ray triangle ΔFB0B2 satisfies the following condition: FB0=H' and B0B2=D/2, where D is the width of the projection on the X-ray detector 112 by X-rays passing through the selected collimator slit 502. Since the X-ray triangle ΔFO'P2 is similar to ΔFB0B2, the following equation can be obtained O'P2/B0B2=FO'/FB0, i.e., z/h'=(D/2)/H'. Through transformation, the following equation can be obtained:

$$z = \frac{h \times D}{2H' \times \cos(\beta)}. \quad (2)$$

Figure 13:
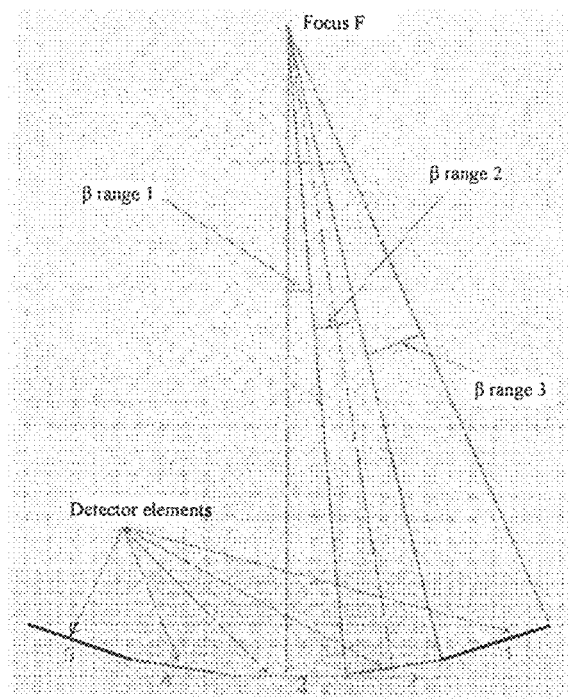

Since an inclination angle α exists between any two adjacent detector elements, in the case where the X-ray detector 112 comprises five detector elements, the offset angle β of the X-ray beam can be divided into three ranges. As shown in FIG. 13, the offset angle range for the X-ray beam projected to the area between the center of the third detector element and the junction of the third and second detector elements is set as β range 1, the offset angle range for the X-ray beam projected to the second detector element is set as β range 2, and the offset angle range for the X-ray beam projected to the first detector element is set as β range 3.

Figure 14:
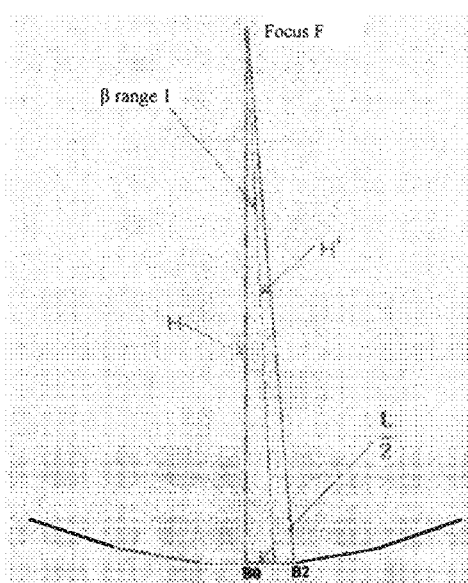

FIG. 14 shows the circumstance where the offset angle β of the X-ray beam is within the range 1. As shown in FIG. 14, the obtained X-ray triangle ΔFB0B2 satisfies the following conditions: FB0=H, B0B2=L/2, and tan(β)=B0B2/FB0=(L/2)/H, wherein L is the length of an individual detector element. Therefore, the range of the offset angle β in the range 1 can be determined as $$0 \leq \beta \leq \mathrm{atan}\left(\frac{\frac{L}{2}}{H}\right).$$

Figure 15:
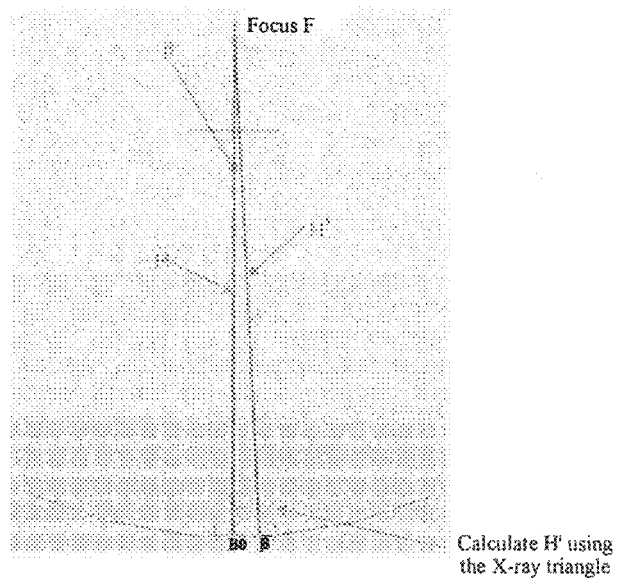

FIG. 15 shows an X-ray triangular ΔFB0B constructed according to the X-ray beam having the offset angle β. Using such an X-ray triangle, the distance from the focus F to the detector element D3 for the X-ray beam having the offset angle β can be calculated as follows:

$$H' = \frac{H}{\cos(\beta)},$$

wherein, $$0 \leq \beta \leq \mathrm{atan}\left(\frac{\frac{L}{2}}{H}\right).$$

Figure 16:
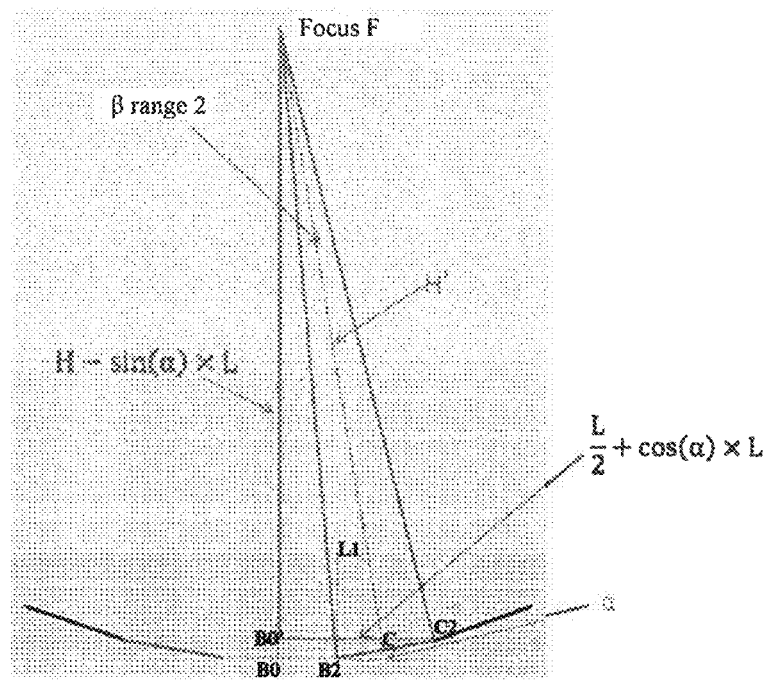

FIG. 16 shows the circumstance where the offset angle β of the X-ray beam is within the range 2. As shown in FIG. 16, C2 is the edge point of the detector element D2, C is the projection point on the detector element D2 formed by the X-ray beam whose offset angle β is within the range 2. An X-ray triangle ΔFB0'C2 can be constructed according to the X-ray beam projected to the point C2, wherein line B0'C2 is parallel to line B0B2. Since there is an inclination angle α between the detector elements D3 and D2, the angle between the extension line of line B0B2 and line B2C2 is α, and the angle between line B0'C2 and line B2C2 or CC2 is also α. With the aid of a straight line L1 passing point B2 and perpendicular to lines B0'C2 (and line B0B2), it can be determined that B0'C2=L/2+cos(α)×L, and FB0'=H-sin(α)×L, where L is the length of an individual detector element. Thereby, it can be determined that the range of the offset angle β of the X-ray beam in the range 2 is:

$$\operatorname{atan}\left(\frac{\frac{L}{2}}{H}\right) < \beta \leq \operatorname{atan}\left(\frac{\frac{L}{2}+\cos(\alpha)\times L}{H-\sin(\alpha)\times L}\right).$$

Figure 17:
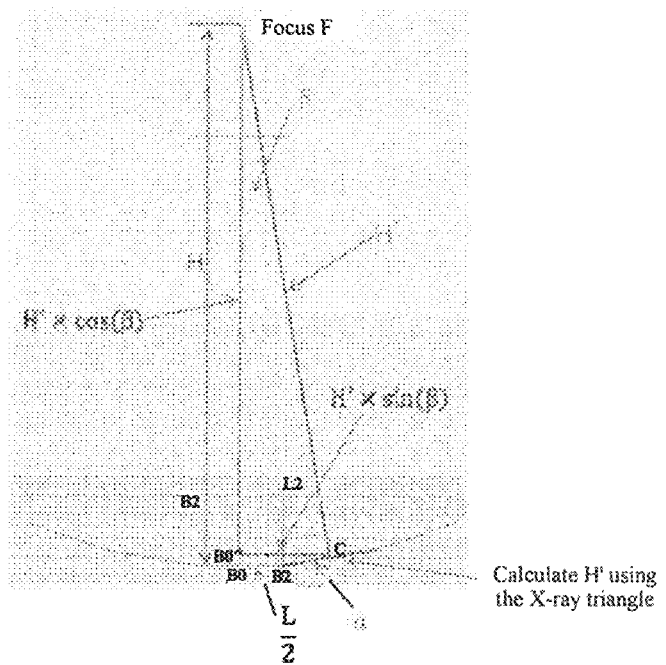

FIG. 17 shows the circumstance where the offset angle β of the X-ray beam is within the range 2, where point C is the projection point of the X-ray beam having the offset angle β on the second detector element, and the distance from the focus F to the second detector element is H'. As shown in FIG. 17, in the obtained X-ray triangle ΔFB0"C, the following conditions are satisfied: FB0"=H'×cos(β), B0"C=H'×sin(β), and, FC=H'. Assume that the length of line B2C is L', then using a line L2 passing point B2 and perpendicular to line B0B2 and B0"C, the following equations can be obtained:

FB0"=FB0−B0"B0=H−sin(α)×L',namely,H'× cos(β)=H−sin(α)×L',and

B0"C=L/2+cos(α)×L',namely,H'×sin(β)=L/2+cos(α)× L'.

Based on the above two equations, it can be determined that the distance H' from the focus F to the detector element 2 for the X-ray beam having the offset angle β is as follows:

$$H' = \frac{H + \frac{L\times\tan(\alpha)}{2}}{\tan(\alpha)\times\sin(\beta)+\cos(\beta)},$$

wherein $$\operatorname{atan}\left(\frac{\frac{L}{2}}{H}\right) < \beta \leq \operatorname{atan}\left(\frac{\frac{L}{2}+\cos(\alpha)\times L}{H-\sin(\alpha)\times L}\right).$$

Figure 18:
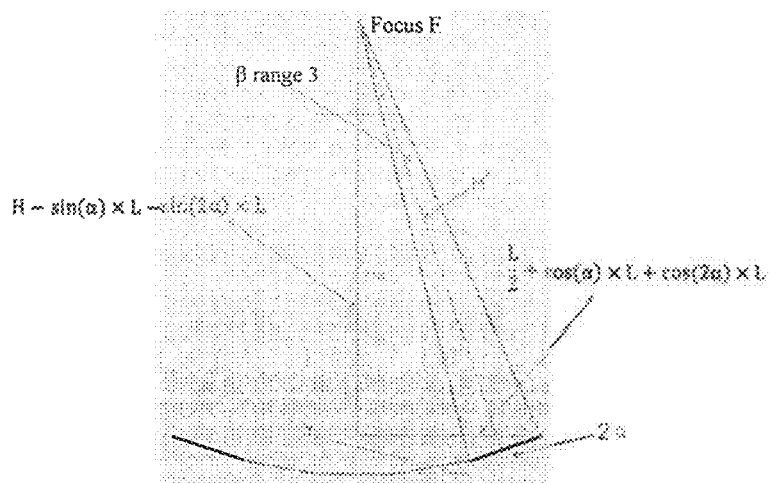
Figure 19:
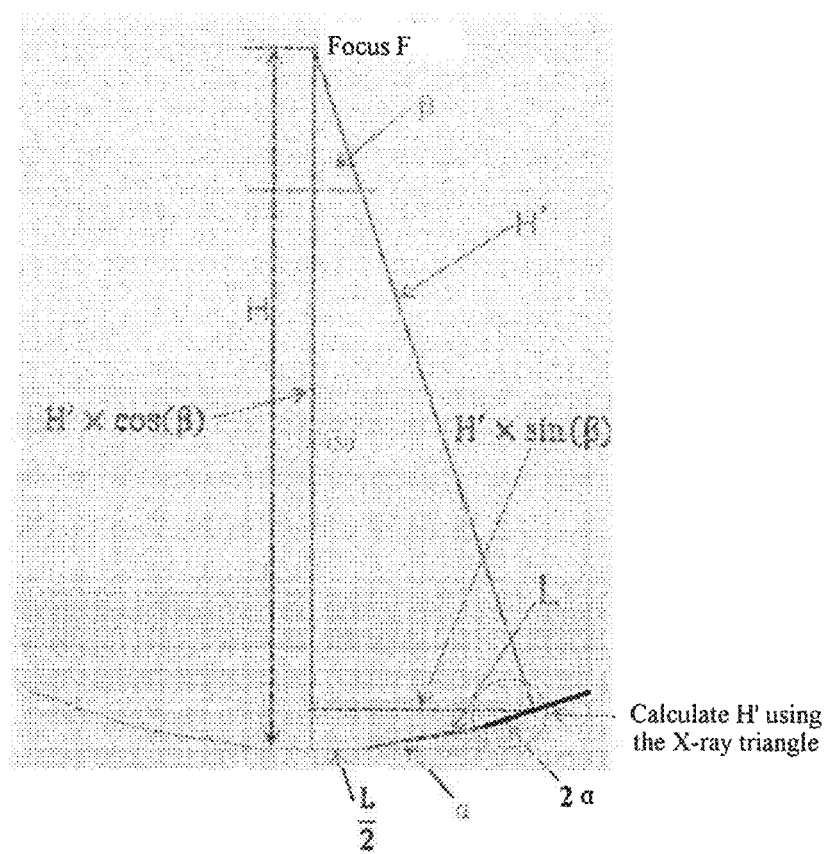

FIGS. 18 and 19 show the circumstances where the offset angle β of the X-ray beam is within the range 3. By adopting a method similar to those used for the ranges 1 and 2, the range of the offset angle β of the X-ray beam in the range 3 can be determined as $$\operatorname{atan}\left(\frac{\frac{L}{2}+\cos(\alpha)\times L}{H-\sin(\alpha)\times L}\right) < \beta \leq \operatorname{atan}\left(\frac{\frac{L}{2}+\cos(\alpha)\times L+\cos(2\alpha)\times L}{H-\sin(\alpha)\times L-\sin(2\alpha)\times L}\right).$$

Besides, an intermediate equation $$\tan(2\alpha) = \frac{H - H'\times\cos(\beta) - L\times\sin(\alpha)}{H'\times\sin(\beta) - \frac{L}{2} - L\times\cos(\alpha)}$$

can be used to determine the distance H' from the focus F to the detector element 1 for the X-ray beam having the offset angle β:

$$H' = \frac{H - L\times\sin(\alpha) + \frac{L\times\tan(2\alpha)}{2} + L\times\cos(\alpha)\times\tan(2\alpha)}{\tan(2\alpha)\times\sin(\beta)+\cos(\beta)},$$

wherein $$\operatorname{atan}\left(\frac{\frac{L}{2}+\cos(\alpha)\times L}{H-\sin(\alpha)\times L}\right) < \beta \leq \operatorname{atan}\left(\frac{\frac{L}{2}+\cos(\alpha)\times L+\cos(2\alpha)\times L}{H-\sin(\alpha)\times L-\sin(2\alpha)\times L}\right).$$

Figure 20:
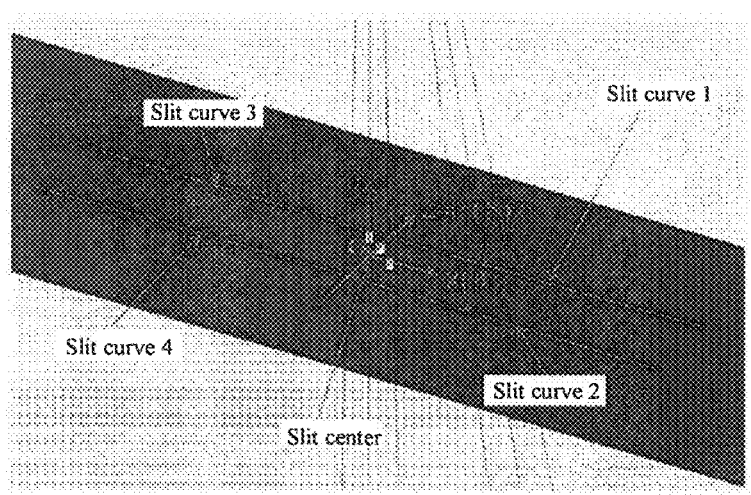

As shown in FIG. 20, because the two opposite edges in the slit longitudinal direction of the collimator slit 502 are symmetrically distributed relative to the axis OX, given a three-dimensional coordinate system XYZ established at the center O of the slit, the slit curves 1 and 2 corresponding to one detector element are symmetrically distributed relative to the axis OX, and the slit curves 3 and 4 corresponding to another detector element are symmetrically distributed relative to the axis OX, namely:

(1) the distribution of the points on slit curve 1 in the plane XOZ satisfies the following equations:

$$x(\beta) = \tan(\beta)\times h$$
$$P(\beta) = \frac{h\times D}{2H'\times\cos(\beta)};$$

(2) the distribution of the points on slit curve 2 in the plane XOZ satisfies the following equations:

$$x(\beta) = \tan(\beta)\times h$$
$$P(\beta) = \frac{h\times D}{2H'\times\cos(\beta)};$$

(3) the distribution of the points on slit curve 3 in the plane XOZ satisfies the following equations:

$$x(\beta) = -\tan(\beta)\times h$$
$$P(\beta) = \frac{h\times D}{2H'\times\cos(\beta)}; \text{ and}$$

(4) the distribution of the points on slit curve 4 in the plane XOZ satisfies the following equations:

$$x(\beta) = -\tan(\beta)\times h$$
$$P(\beta) = -\frac{h\times D}{2H'\times\cos(\beta)}.$$

Therefore, in the case where the X-ray detector 112 comprises five identical detector elements and the inclination angles between any two adjacent detector elements are equal, given a three-dimensional coordinate system XYZ established at the center of the collimator slit 502, the distribution of the two opposite edges along the longitudinal direction of the slit in the two-dimensional plane XOZ can be determined according to the following equation:

$$\begin{cases} x(\beta) = \pm \tan(\beta) \times h \\ P(\beta) = \pm \dfrac{h \times D}{2H' \times \cos(\beta)} \end{cases} \quad (3)$$

wherein:

when $0 \le \beta \le \mathrm{atan}\left(\dfrac{\dfrac{L}{2}}{H}\right)$, $H' = \dfrac{H}{\cos(\beta)}$;  (1)

when $\mathrm{atan}\left(\dfrac{\dfrac{L}{2}}{H}\right) < \beta \le \mathrm{atan}\left(\dfrac{\dfrac{L}{2} + \cos(\alpha) \times L}{H - \sin(\alpha) \times L}\right)$,  (2)

$H' = \dfrac{H + \dfrac{L \times \tan(\alpha)}{2}}{\tan(\alpha) \times \sin(\beta) + \cos(\beta)}$; and when $\mathrm{atan}\left(\dfrac{\dfrac{L}{2} + \cos(\alpha) \times L}{H - \sin(\alpha) \times L}\right) <$  (3)

$\beta \le \mathrm{atan}\left(\dfrac{\dfrac{L}{2} + \cos(\alpha) \times L + \cos(2\alpha) \times L}{H - \sin(\alpha) \times L - \sin(2\alpha) \times L}\right)$, $H' = \dfrac{H - L \times \sin(\alpha) + \dfrac{L \times \tan(2\alpha)}{2} + L \times \cos(\alpha) \times \tan(2\alpha)}{\tan(2\alpha) \times \sin(\beta) + \cos(\beta)}$.

While an exemplary embodiment of the present invention has been described above using an example where the X-ray detector 112 comprises five identical detector elements and where any two adjacent detector elements have an equal inclination angle, it will be appreciated by persons skilled in the art that the present invention is not limited to this particular embodiment.

FIG. 2 shows a circumstance where the X-ray detector 112 comprises seven identical detector elements and where the inclination angles between any two adjacent detector elements are equal. As shown in FIG. 2, the seven detector elements are divided into four detector segments, wherein the center of the detector element corresponding to the detector segment 1, the center of the selected collimator slit 502 and the focus F of the X-ray tube are in a straight line perpendicular to the detector element corresponding to the detector segment 1 and the selected collimator slit 502. Assume that the length of each detector element is L, the width of the projection on the X-ray detector 112 by the X-rays passing through the selected collimator slit 502 is D, the vertical distance from the focus of the X-ray tube to the X-ray detector 112 is H, the vertical distance from the focus of the X-ray tube to the selected collimator slit 502 is h, the inclination angle between any two adjacent detector elements is α, the offset angle of the X-ray beam relative to a plane passing the focus F of the X-ray tube and perpendicular to the collimator slit plane is β, and the distance of the X-ray beam having the offset angle β from the focus F of the X-ray tube to its projection point on the X-ray detector 112 is H', given a three-dimensional coordinate system XYZ established at the center of the collimator slit 502, as shown in FIG. 5, then the distribution of the two opposite edges of the collimator slit 502 in the slit longitudinal direction in the two-dimensional plane XOZ can be determined according to the following equation:

$$\begin{cases} x(\beta) = \pm \tan(\beta) \times h \\ P(\beta) = \pm \dfrac{h \times D}{2H' \times \cos(\beta)} \end{cases} \quad (4)$$

wherein, (1) when $$0 \le \beta \le \mathrm{atan}\left(\dfrac{\dfrac{L}{2}}{H}\right),$$

namely, when the projection of the X-ray beam on the X-ray detector 112 is located in the detector segment 1 as shown in FIG. 2, $$H' = \dfrac{H}{\cos(\beta)};$$

(2) when $$\mathrm{atan}\left(\dfrac{\dfrac{L}{2}}{H}\right) < \beta \le \mathrm{atan}\left(\dfrac{\dfrac{L}{2} + \cos(\alpha) \times L}{H - \sin(\alpha) \times L}\right),$$

namely, when the projection of the X-ray beam on the X-ray detector 112 is located in the detector segment 2 as shown in FIG. 2, $$H' = \dfrac{H + \dfrac{L \times \tan(\alpha)}{2}}{\tan(\alpha) \times \sin(\beta) + \cos(\beta)};$$

(3) when $$\mathrm{atan}\left(\dfrac{\dfrac{L}{2} + \cos(\alpha) \times L}{H - \sin(\alpha) \times L}\right) < \beta \le \mathrm{atan}\left(\dfrac{\dfrac{L}{2} + \cos(\alpha) \times L + \cos(2\alpha) \times L}{H - \sin(\alpha) \times L - \sin(2\alpha) \times L}\right),$$

namely, when the projection of the X-ray beam on the X-ray detector 112 is located in the detector segment 3 as shown in FIG. 2, $$H' = \dfrac{H - L \times \sin(\alpha) + \dfrac{L \times \tan(2\alpha)}{2} + L \times \cos(\alpha) \times \tan(2\alpha)}{\tan(2\alpha) \times \sin(\beta) + \cos(\beta)};$$

and (4) when $$\mathrm{atan}\left(\dfrac{\dfrac{L}{2} + \cos(\alpha) \times L + \cos(2\alpha) \times L}{H - \sin(\alpha) \times L - \sin(2\alpha) \times L}\right) < \beta \le$$

$$\mathrm{atan}\left(\dfrac{\dfrac{L}{2} + \cos(\alpha) \times L + \cos(2\alpha) \times L + \cos(3\alpha) \times L}{H - \sin(\alpha) \times L - \sin(2\alpha) \times L - \sin(3\alpha) \times L}\right),$$

namely, when the projection of the X-ray beam on the X-ray detector 112 is located in the detector segment 4 as shown in FIG. 2, $$H' = \frac{H - L \times \sin(\alpha) - L \times \sin(2\alpha) + \frac{L \times \tan(3\alpha)}{2} + L \times \cos(\alpha) \times \tan(3\alpha) + L \times \cos(2\alpha) \times \tan(3\alpha)}{\tan(3\alpha) \times \sin(\beta) + \cos(\beta)}.$$

The left part of FIG. 3 shows a circumstance where the X-ray detector 112 comprises six identical detector elements and where the inclination angles between any two adjacent detector elements are equal. As shown in the left part of FIG. 3, the six detector elements are divided into four detector segments, wherein the center of the detector element corresponding to the detector segment 1, the center of the selected collimator slit 502 and the focus of the X-ray tube are in a straight line, which is perpendicular to the detector element corresponding to the detector segment 1 and the selected collimator slit 502. Assume that the length of each detector element is L, the width of the projection on the X-ray detector 112 by X-rays passing through the selected collimator slit 502 is D, the vertical distance from the focus of the X-ray tube to the X-ray detector 112 is H, the vertical distance from the focus of the X-ray tube to the selected collimator slit 502 is h, the inclination angle between any two adjacent detector elements is $\alpha$, the offset angle of the X-ray beam relative to a plane passing the focus F of the X-ray tube and perpendicular to the collimator slit plane is $\beta$, the distance of the X-ray beam having the offset angle $\beta$ from the focus F of the X-ray tube to its projection point on the X-ray detector is H', given a three-dimensional coordinate system XYZ established at the center of the collimator slit 502, as shown in FIG. 5, then the distribution of the portions of the two opposite edges of the collimator slit 502 along the slit longitudinal direction corresponding to the detector segments 1-3 as shown in the left of FIG. 3 in the two-dimensional plane XOZ can be determined according to the following equation:

$$\begin{cases} x(\beta) = \pm \tan(\beta) \times h \\ P(\beta) = \pm \dfrac{h \times D}{2H' \times \cos(\beta)}, \end{cases} \quad (5\text{-}1)$$

(1) when $$0 \le \beta \le \mathrm{atan}\!\left(\frac{\frac{L}{2}}{H}\right),$$

namely, when the projection of the X-ray beam on the X-ray detector 112 is located in the detector segment 1 as shown in the left of FIG. 3, $$H' = \frac{H}{\cos(\beta)};$$

(2) when $$\mathrm{atan}\!\left(\frac{\frac{L}{2}}{H}\right) < B \le \mathrm{atan}\!\left(\frac{\frac{1}{2} + \cos(\alpha) \times L}{H - \sin(\alpha) \times L}\right),$$

namely, when the projection of the X-ray beam on the X-ray detector 112 is located in the detector segment 2 as shown in the left of FIG. 3, $$H' = \frac{H + \dfrac{L \times \tan(\alpha)}{2}}{\tan(\alpha) \times \sin(\beta) + \cos(\beta)};$$

and
(3) when $$\mathrm{atan}\!\left(\frac{\frac{L}{2} + \cos(\alpha) \times L}{H - \sin(\alpha) \times L}\right) < \beta \le \mathrm{atan}\!\left(\frac{\frac{L}{2} + \cos(\alpha) \times L + \cos(2\alpha) \times L}{H - \sin(\alpha) \times L - \sin(2\alpha) \times L}\right),$$

namely, when the projection of the X-ray beam on the X-ray detector 112 is located in the detector segment 3 as shown in the left of FIG. 3, $$H' = \frac{H - L \times \sin(\alpha) + \dfrac{L \times \tan(2\alpha)}{2} + L \times \cos(\alpha) \times \tan(2\alpha)}{\tan(2\alpha) \times \sin(\beta) + \cos(\beta)}.$$

Similarly, the distribution of the portions of the two opposite edges of the collimator slit 502 corresponding to the detector segment 4 as shown in the left of FIG. 3 in the two-dimensional plane XOZ can be determined according to the following equation:

$$\begin{cases} X(\beta) = \tan(\beta) \times h \\ P(\beta) = \dfrac{h \times D}{2H' \times \cos(\beta)}, \end{cases} \quad (5\text{-}2)$$

wherein, $$\mathrm{atan}\!\left(\frac{\frac{L}{2} + \cos(\alpha) \times L + \cos(2\alpha) \times L}{H - \sin(\alpha) \times L - \sin(2\alpha) \times L}\right) < \beta \le$$

$$\mathrm{atan}\!\left(\frac{\frac{L}{2} + \cos(\alpha) \times L + \cos(2\alpha) \times L + \cos(3\alpha) \times L}{H - \sin(\alpha) \times L - \sin(2\alpha) \times L - \sin(3\alpha) \times L}\right),$$

and $$H' = \frac{H - L \times \sin(\alpha) - L \times \sin(2\alpha) + \dfrac{L \times \tan(3\alpha)}{2} + L \times \cos(\alpha) \times \tan(3\alpha) + L \times \cos(2\alpha) \times \tan(3\alpha)}{\tan(3\alpha) \times \sin(\beta) + \cos(\beta)}.$$

The left part of FIG. 4 shows a circumstance where the X-ray detector 112 comprises four identical detector elements and where the inclination angles between any two adjacent detector elements are equal. As shown in the left part of FIG. 4, the four detector elements are divided into three detector segments, wherein the center of the detector element corresponding to the detector segment 1, the center of the selected collimator slit 502 and the focus of the X-ray tube are in a straight line which is perpendicular to the detector element corresponding to the detector segment 1 and the selected collimator slit 502. Assume that the length of each detector element is L, the width of the projection on the X-ray detector 112 by X-rays passing through the selected collimator slit 502 is D, the vertical distance from the focus of the X-ray tube to the X-ray detector 112 is H, the vertical distance from the focus of the X-ray tube to the selected collimator slit 502 is h, the inclination angle between any two adjacent detector elements is α, the offset angle of the X-ray beam relative to a plane passing the focus F of the X-ray tube and perpendicular to the collimator slit plane is β, the distance of the X-ray beam having the offset angle β from the focus F of the X-ray tube to its projection point on the X-ray detector is H', given a three-dimensional coordinate system XYZ established at the center of the collimator slit 502 as shown in FIG. 5, then the distribution of the portions of the two opposite edges of the collimator slit 502 along the slit longitudinal direction corresponding to the detector segments 1-2 as shown in the left of FIG. 4 in the two-dimensional plane XOZ can be determined according to the following equation:

$$\begin{cases} X(\beta) = \pm \tan(\beta) \times h \\ P(\beta) = \pm \dfrac{h \times D}{2H' \times \cos(\beta)}, \end{cases} \quad (6\text{-}1)$$

wherein,
(1) when $$0 \le \beta \le \operatorname{atan}\left(\dfrac{\frac{L}{2}}{H}\right),$$

namely, when the projection of the X-ray beam on the X-ray detector 112 is located in the detector segment 1 as shown in the left of FIG. 4, $$H' = \dfrac{H}{\cos(\beta)},$$

and
(2) when $$\operatorname{atan}\left(\dfrac{\frac{L}{2}}{H}\right) < \beta \le \operatorname{atan}\left(\dfrac{\frac{L}{2} + \cos(\alpha) \times L}{H - \sin(\alpha) \times L}\right),$$

namely, when the projection of the X-ray beam on the X-ray detector 112 is located in the detector segment 2 as shown in the left of FIG. 4, $$H' = \dfrac{H + \dfrac{L \times \tan(\alpha)}{2}}{\tan(\alpha) \times \sin(\beta) + \cos(\beta)}.$$

Similarly, the distribution of the portions of the two opposite edges of the collimator slit 502 corresponding to the detector segment 3 as shown in the left of FIG. 4 in the two-dimensional plane XOZ can be determined according to the following equation:

$$\begin{cases} X(\beta) = \tan(\beta) \times h \\ P(\beta) = \pm \dfrac{h \times D}{2H' \times \cos(\beta)}, \end{cases} \quad (6\text{-}2)$$

wherein $$\operatorname{atan}\left(\dfrac{\frac{L}{2} + \cos(\alpha) \times L}{H - \sin(\alpha) \times L}\right) < \beta \le \operatorname{atan}\left(\dfrac{\frac{L}{2} + \cos(\alpha) \times L + \cos(2\alpha) \times L}{H - \sin(\alpha) \times L - \sin(2\alpha) \times L}\right),$$

and $$H' = \dfrac{H - L \times \sin(\alpha) + \dfrac{L \times \tan(2\alpha)}{2} + L \times \cos(\alpha) \times \tan(2\alpha)}{\tan(2\alpha) \times \sin(\beta) + \cos(\beta)}.$$

The right part of FIG. 4 shows a circumstance where the X-ray detector 112 comprises three identical detector elements and where the inclination angles between any two adjacent detector elements are equal. As shown in the right part of FIG. 4, the three detector elements are divided into two detector segments, wherein the center of the detector element corresponding to the detector segment 1, the center of the selected collimator slit 502 and the focus of the X-ray tube, are in a straight line which is perpendicular to the detector element corresponding to the detector segment 1 and the selected collimator slit 502. Assume that the length of each detector element is L, the width of the projection on the X-ray detector 112 by the X-rays passing through the selected collimator slit 502 is D, the vertical distance from the focus of the X-ray tube to the X-ray detector 112 is H, the vertical distance from the focus of the X-ray tube to the selected collimator slit 502 is h, the inclination angle between any two adjacent detector elements is α, the offset angle of the X-ray beam relative to a vertical plane passing the focus F of the X-ray tube and perpendicular to the collimator slit plane is β, the distance of the X-ray beam having the offset angle β from the focus F of the X-ray tube to its projection point on the X-ray detector is H', given a three-dimensional coordinate system XYZ established at the center of the collimator slit 502 as shown in FIG. 5, then the distribution of the two opposite edges of the collimator slit 502 along the slit longitudinal direction in the two-dimensional plane XOZ can be determined according to the following equation:

$$\begin{cases} X(\beta) = \pm \tan(\beta) \times h \\ P(\beta) = \pm \dfrac{h \times D}{2H' \times \cos(\beta)}, \end{cases} \quad (7)$$

wherein,
(1) when $$0 \le \beta \le \operatorname{atan}\left(\dfrac{\frac{L}{2}}{H}\right),$$

namely, when the projection of the X-ray beam on the X-ray detector 112 is located in the detector segment 1 as shown in the right part of FIG. 4, $$H' = \dfrac{H}{\cos(\beta)},$$

and
(2) when $$\text{atan}\left(\frac{\frac{L}{2}}{H}\right) < \beta \le \text{atan}\left(\frac{\frac{L}{2} + \cos(\alpha) \times L}{H - \sin(\alpha) \times L}\right),$$

namely, when the projection of the X-ray beam on the X-ray detector 112 is located in the detector segment 2 as shown in the right part of FIG. 4, $$H' = \frac{H + \frac{L \times \tan(\alpha)}{2}}{\tan(\alpha) \times \sin(\beta) + \cos(\beta)}.$$

Thus, the distribution of the two opposite edges of the selected collimator slit 502 along the slit longitudinal direction in the two-dimensional plane XOZ are jointly determined by the following factors: the vertical distance between the focus F of the X-ray tube 102 and the selected collimator slit 502, the vertical distance between the focus F of the X-ray tube 102 and the X-ray detector 112, the inclination angle between any two adjacent detector elements in the X-ray detector 112, the length of each detector element in the X-ray detector 112, the width of the projection on the X-ray detector 112 by X-rays passing through the selected collimator slit 502, and the offset angle of the connecting lines from the various points on the longitudinal center line of the selected collimator slit to the focus F of the X-ray tube relative to a plane perpendicular to the selected collimator slit 502 and passing the focus F of the X-ray tube. Correspondingly, based on the distribution of the two longitudinal edges of the selected collimator slit 502 in the two-dimensional plane XOZ, the width distribution of the selected collimator slit 502 in the longitudinal direction can be determined.

In the present field, it is conventional to calculate the distribution of the two longitudinal edges of the collimator slit 502 in the two-dimensional plane XOZ using the following general formula for the collimator slit profile, based on the width D of the X-ray beam projected onto the X-ray detector 112, the vertical distance H between the focus F of the X-ray tube 102 and the X-ray detector 112, the vertical distance h between the focus F of the X-ray tube 102 and the collimator slit 502:

$$P(x) = \pm \frac{D}{2H} \times \sqrt{x^2 + h^2}.$$

Figure 21:
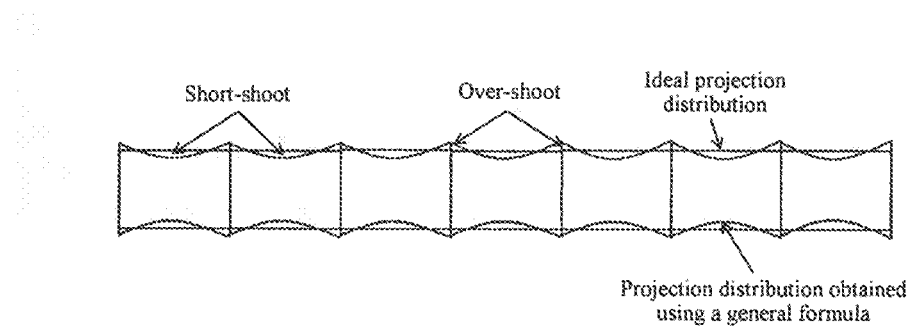
FIG. 21 shows a projection distribution on a radiation detector obtained by using a collimator where the slit is determined by using a general formula for a CT collimator slit profile.

Because such an equation does not take into account the specific dimensions of the various detector elements in the X-ray detector 112 and the positional relationship therebetween, the X-ray beam projected to the X-ray detector 112 through a collimator where the distribution of the two longitudinal edges of the slit thereof satisfies the above equation forms, an undulated, curved projection distribution, as shown in FIG. 21, is produced. As compared with the ideal, beeline projection distribution, the curved, actual projection distribution contains a plurality of over-shoot areas and short-shoot areas. The over-shoot will cause the subject to receive extra radiation dose and the short-shoot will result in a detection error(s).

Figure 22:
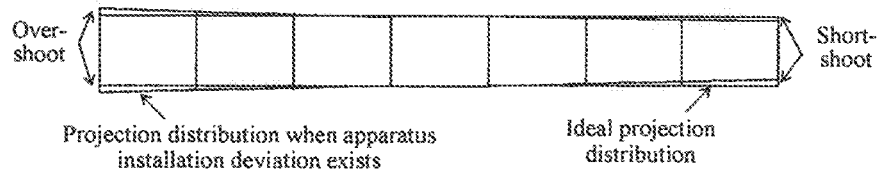
FIG. 22 illustrates a projection distribution on a radiation detector obtained by using a collimator according to an exemplary embodiment of the present invention under the circumstance where there is an apparatus installation deviation.

In the collimator according to the present invention, the distribution of the two opposite edges of each slit 502 along the slit longitudinal direction in the two-dimensional plane XOZ takes into account not only the conventional parameters, but also the structural and positional relationship between the individual detector elements in the X-ray detector 112. Therefore, without consideration of the apparatus installation deviation, the actual projection distribution of the X-ray beam projected onto the X-ray detector 112 through such a collimator will be completely equal to the ideal, rectangular projection distribution. Even if an installation deviation exists, it will just cause a small amount of short-shoot and over-shoot areas at the two ends of the X-ray detector 112, as shown in FIG. 22. FIG. 22 shows the circumstance where the X-ray detector 112 includes seven detector elements and installation deviation exists.

Figure 23:
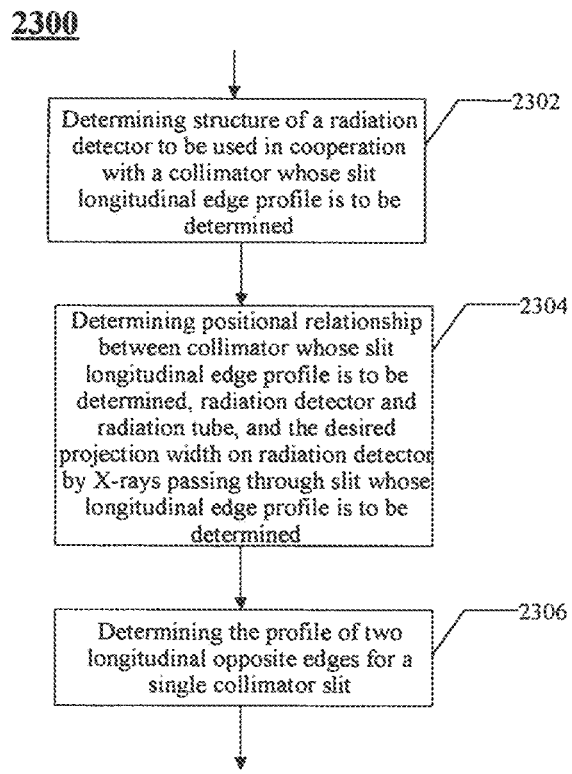
FIG. 23 shows a method of determining the profile of two longitudinal edges of a single slit of a collimator according to an exemplary embodiment of the present invention.

FIG. 23 shows a flowchart 2300 of a method for determining the distribution of the longitudinal edges of a collimator slit according to an exemplary embodiment of the present invention. The collimator comprises a planar gating device. The gating device is provided with one or more slits. The plurality of slits is aligned in parallel in the slit longitudinal direction and has different average widths to meet different detection requirements, as shown in FIG. 5A.

As shown in FIG. 23, at step 2302, the structure of an X-ray detector to be used in cooperation with a collimator whose slit longitudinal edge profile is to be determined is determined. The X-ray detector may comprise a plurality of plate detector elements arranged in a row, and there is an inclination angle between two adjacent detector elements. More particularly, the number of the detector elements may be 3-7. The plurality of X-ray detector elements forming the X-ray detector may have the same or different width and the same or different length. The inclination angles between two adjacent detector elements may be the same or different. The width of the projection on the X-ray detector by X-rays passing through the collimator slit having the largest average width is equal to or less than the width of the X-ray detector, and the length of the projection on the X-ray detector by X-rays passing through the slit having the largest length is equal to or less than the length of the X-ray detector, as shown in FIG. 7.

For ease of illustration, the circumstance where the X-ray detector comprises a plurality of identical detector elements and where the inclination angles between any two adjacent detector elements are equal is used as an example to describe the method 2300 according to an exemplary embodiment of the present invention.

The steps of determining the structure of the X-ray detector comprises: determining the length L of the detector elements of the X-ray detector and the desired width D of projection on the X-ray detector formed by X-rays passing through the collimator slit whose longitudinal edge profile is to be determined, and determining the inclination angle α between any two adjacent detector elements.

At step 2304, a determination is made as to the positional relationship between the collimator whose slit longitudinal edge profile is to be determined, the X-ray detector and the X-ray tube, and the desired projection width on the radiation detector formed by X-rays passing through the collimator slit whose longitudinal edge profile is to be determined. The determination includes determining a vertical distance h between the focus F of the X-ray tube and the collimator whose slit longitudinal edge profile is to be determined, determining a vertical distance H between the focus F of the X-ray tube and the X-ray detector, and establishing a three-dimensional coordinate system XYZ at the center of the slit of the collimator whose slit longitudinal edge profile is to be determined, as shown in FIG. 5. A connecting line from the focus F of the X-ray tube to the center O of the collimator slit whose longitudinal edge profile is to be determined is perpendicular to the plane of the collimator slit, and an extension line of said connecting line is perpendicular to one detector element in the X-ray detector, as shown in FIG. 7

Step 2304 further includes determining which detector element of the X-ray detector is perpendicular to the axis OY in the three-dimensional coordinate system. For an X-ray detector comprising an odd number of detector elements such as 3, 5 and 7 detector elements, the middle detector element may be determined to be perpendicular to the axis OY. For an X-ray detector comprising an even number of detector elements such as 4 and 6 detector elements, the middle left or middle right detector element may be determined to be perpendicular to the axis OY, as shown in FIG. 2-4.

At step 2306, the distribution of the two opposite longitudinal edges of the collimator slit whose longitudinal edge profile is to be determined in the two-dimensional plane XOZ can be determined based on the following: the vertical distance h between the focus F of the X-ray tube and the collimator whose slit longitudinal edge profile is to be determined, the vertical distance H between the focus F of the X-ray tube 102 and the X-ray detector, the length L of each detector element in the X-ray detector, the desired width D of the projection on the X-ray detector by X-rays passing through the collimator whose slit longitudinal edge profile is to be determined, and the inclination angle between adjacent detector elements in the X-ray detector.

Step 2306 includes: determining the offset angle $\beta$ of the various points on the OX axis relative to the two-dimensional plane YOZ, calculating the distance H' from the focus of the X-ray tube to the X-ray detector through the various points on the OX axis based on the determined offset angle, and determining, at least according to the offset angle $\beta$ and the determined H', the profile of the two opposite longitudinal edges of the collimator slit that is required to be determined.

Specifically, in the case where the X-ray detector comprises five detector elements and where two adjacent detector elements have an equal inclination angle, as shown in the right part of FIG. 3, the five detector elements are divided into three detector segments 1, 2 and 3. As shown in FIG. 13, the offset angle $\beta$ corresponding to the right half of the detector segments 1, 2, and 3 have three different value ranges due to the different detector elements, namely, $\beta$ range 1, $\beta$ range 2 and $\beta$ range 3, wherein:

(1) for $\beta$ range 1, $$0 \leq \beta \leq \mathrm{atan}\left(\frac{\frac{L}{2}}{H}\right);$$

(2) for $\beta$ range 2, $$\mathrm{atan}\left(\frac{\frac{L}{2}}{H}\right) < \beta \leq \mathrm{atan}\left(\frac{\frac{L}{2} + \cos(\alpha) \times L}{H - \sin(\alpha) \times L}\right);$$

and
(3) for $\beta$ range 3, $$\mathrm{atan}\left(\frac{\frac{L}{2} + \cos(\alpha) \times L}{H - \sin(\alpha) \times L}\right) < \beta \leq \mathrm{atan}\left(\frac{\frac{L}{2} + \cos(\alpha) \times L + \cos(2\alpha) \times L}{H - \sin(\alpha) \times L - \sin(2\alpha) \times L}\right).$$

After the value ranges of the offset angle $\beta$ have been determined, as shown in FIGS. 14-19, the distance H' from the focus of the X-ray tube to the X-ray detector through the various points on the OX axis, may be determined according to the following equations:

$$H' = \frac{H}{\cos(\beta)}, \text{ wherein } 0 < \beta \leq \mathrm{atan}\left(\frac{\frac{L}{2}}{H}\right); \tag{1}$$

$$H' = \frac{H + \frac{L \times \tan(\alpha)}{2}}{\tan(\alpha) \times \sin(\beta) + \cos(\beta)}, \text{ wherein} \tag{2}$$

$$\mathrm{atan}\left(\frac{\frac{L}{2}}{H}\right) < \beta \leq \mathrm{atan}\left(\frac{\frac{L}{2} + \cos(\alpha) \times L}{H - \sin(\alpha) \times L}\right); \text{ and}$$

$$H' = \frac{H - L \times \sin(\alpha) + \frac{L \times \tan(2\alpha)}{2} + L \times \cos(\alpha) \times \tan(2\alpha)}{\tan(2\alpha) \times \sin(\beta) + \cos(\beta)}, \tag{3}$$

wherein $\mathrm{atan}\left(\frac{\frac{L}{2} + \cos(\alpha) \times L}{H - \sin(\alpha) \times L}\right) <$ $$\beta \leq \mathrm{atan}\left(\frac{\frac{L}{2} + \cos(\alpha) \times L + \cos(2\alpha) \times L}{H - \sin(\alpha) \times L - \sin(2\alpha) \times L}\right).$$

Since the offset angle $\beta$ corresponding to the left part of the detector segments 1, 2, and 3 is symmetric to the offset angle $\beta$ corresponding to the right part of the detector segments 1, 2, and 3 relative to the two-dimensional plane symmetry YOZ, the value ranges for the offset angle $\beta$ corresponding to the left part of the detector segments 1, 2, and 3 and the corresponding H' can be determined in a similar manner.

Thereafter, the profile of the two longitudinal opposite edges of the collimator slit can be determined according to the following equation based on the offset angle $\beta$ and H':

$$\begin{cases} X(\beta) = \pm \tan(\beta) \times h \\ P(\beta) = \pm \frac{h \times D}{2H' \times \cos(\beta)} \end{cases}.$$

For the case where the X-ray detector comprises three identical detector elements and two adjacent detector elements have an equal inclination angle, as shown in the right part of FIG. 4, the three detector elements are divided into detector segments 1 and 2. Similarly, the offset angle $\beta$ corresponding to the right half of the detector segments 1 and 2 have two different value ranges due to different detector elements, namely, $\beta$ range 1 and $\beta$ range 2, wherein:

(1) for $\beta$ range 1, $$0 \leq \beta \leq \mathrm{atan}\left(\frac{\frac{L}{2}}{H}\right);$$

and
(2) for $\beta$ range 2, $$\mathrm{atan}\left(\frac{\frac{L}{2}}{H}\right) < \beta \leq \mathrm{atan}\left(\frac{\frac{L}{2} + \cos(\alpha) \times L}{H - \sin(\alpha) \times L}\right).$$

After the value ranges of the offset angle β have been determined, the distance H' from the focus of the X-ray tube to the X-ray detector through the various points on the OX axis may be determined according to the following equations:

$$H' = \frac{H}{\cos(\beta)}, \text{ wherein } 0 \leq \beta \leq \text{atan}\left(\frac{\frac{L}{2}}{H}\right); \text{ and} \quad (1)$$

$$H' = \frac{H + \frac{L \times \tan(\alpha)}{2}}{\tan(\alpha) \times \sin(\beta) + \cos(\beta)}, \quad (2)$$

$$\text{wherein atan}\left(\frac{\frac{L}{2}}{H}\right) < \beta \leq \text{atan}\left(\frac{\frac{L}{2} + \cos(\alpha) \times L}{H - \sin(\alpha) \times L}\right).$$

Since the offset angle β corresponding to the left part of the detector segments 1 and 2 is symmetric to the offset angle β corresponding to the right part of the detector segments 1 and 2 relative to the two-dimensional plane symmetry YOZ, the value ranges for the offset angle β corresponding to the left part of the detector segments 1 and 2 and the corresponding H' can be determined in a similar manner.

Thereafter, the profile of the two longitudinal opposite edges of the collimator slit can be determined according to the following equation based on the offset angle β and H':

$$\begin{cases} X(\beta) = \pm \tan(\beta) \times h \\ P(\beta) = \pm \frac{h \times D}{2H' \times \cos(\beta)} \end{cases}.$$

For the case where the X-ray detector comprises seven identical detector elements and two adjacent detector elements have an equal inclination angle, as shown in FIG. 2, the seven detector elements are divided into four detector segments 1, 2, 3 and 4. Similarly, the offset angle β corresponding to the right half of the detector segments 1, 2, 3 and 4 have four different value ranges due to the different detector elements, namely, β range 1, β range 2, β range 3, and β range 4, wherein:

(1) for β range 1, $$0 \leq \beta \leq \text{atan}\left(\frac{\frac{L}{2}}{H}\right);$$

(2) for β range 2, $$\text{atan}\left(\frac{\frac{L}{2}}{H}\right) < \beta \leq \text{atan}\left(\frac{\frac{L}{2} + \cos(\alpha) \times L}{H - \sin(\alpha) \times L}\right);$$

(3) for β range 3, $$\text{atan}\left(\frac{\frac{L}{2} + \cos(\alpha) \times L}{H - \sin(\alpha) \times L}\right) < \beta \leq \text{atan}\left(\frac{\frac{L}{2} + \cos(\alpha) \times L + \cos(2\alpha) \times L}{H - \sin(\alpha) \times L - \sin(2\alpha) \times L}\right);$$

(4) for β range 4, $$\text{atan}\left(\frac{\frac{L}{2} + \cos(\alpha) \times L + \cos(2\alpha) \times L}{H - \sin(\alpha) \times L - \sin(2\alpha) \times L}\right) < \beta \leq$$

$$\text{atan}\left(\frac{\frac{L}{2} + \cos(\alpha) \times L + \cos(2\alpha) \times L + \cos(3\alpha) \times L}{H - \sin(\alpha) \times L - \sin(2\alpha) \times L - \sin(3\alpha) \times L}\right).$$

After the value ranges of the offset angle β have been determined, the distance H' from the focus of the X-ray tube to the X-ray detector through the various points on the OX axis may be determined according to the following equations:

$$H' = \frac{H}{\cos(\beta)}, \text{ where } 0 \leq \beta \leq \text{atan}\left(\frac{\frac{L}{2}}{H}\right); \quad (1)$$

$$H' = \frac{H + \frac{L \times \tan(\alpha)}{2}}{\tan(\alpha) \times \sin(\beta) + \cos(\beta)}, \quad (2)$$

$$\text{where atan}\left(\frac{\frac{L}{2}}{H}\right) < \beta \leq \text{atan}\left(\frac{\frac{L}{2} + \cos(\alpha) \times L}{H - \sin(\alpha) \times L}\right);$$

$$H' = \frac{H - L \times \sin(\alpha) + \frac{L \times \tan(2\alpha)}{2} + L \times \cos(\alpha) \times \tan(2\alpha)}{\tan(2\alpha) \times \sin(\beta) + \cos(\beta)}, \text{ where} \quad (3)$$

$$\text{atan}\left(\frac{\frac{L}{2} + \cos(\alpha) \times L}{H - \sin(\alpha) \times L}\right) < \beta \leq \text{atan}\left(\frac{\frac{L}{2} + \cos(\alpha) \times L + \cos(2\alpha) \times L}{H - \sin(\alpha) \times -\sin(2\alpha) \times L}\right); \text{ and}$$

$$H' = \frac{H - L \times \sin(\alpha) - L \times \sin(2\alpha) + \frac{L \times \tan(3\alpha)}{2} + L \times \cos(\alpha) \times \tan(3\alpha) + L \times \cos(2\alpha) \times \tan(3\alpha)}{\tan(3\alpha) \times \sin(\beta) + \cos(\beta)}, \quad (4)$$

where $$\text{atan}\left(\frac{\frac{L}{2} + \cos(\alpha) \times L + \cos(2\alpha) \times L}{H - \sin(\alpha) \times L - \sin(2\alpha) \times L}\right) < \beta \leq$$

$$\text{atan}\left(\frac{\frac{L}{2} + \cos(\alpha) \times L + \cos(2\alpha) \times L + \cos(3\alpha) \times L}{H - \sin(\alpha) \times L - \sin(2\alpha) \times L - \sin(3\alpha) \times L}\right).$$

Since the offset angle β corresponding to the left part of the detector segments 1, 2, 3 and 4 is symmetrical to the offset angle β corresponding to the right part of the detector segments 1, 2, 3 and 4, relative to the two-dimensional plane symmetry YOZ, the value ranges for the offset angle β corresponding to the left part of the detector segments 1, 2, 3 and 4 and the corresponding H' can be determined in a similar manner.

Thereafter, the profile of the two longitudinal opposite edges of the collimator slit can be determined according to the following equation based on the offset angle β and H':

$$\begin{cases} X(\beta) = \pm \tan(\beta) \times h \\ P(\beta) = \pm \frac{h \times D}{2H' \times \cos(\beta)} \end{cases}.$$

For the case where the X-ray detector comprises four identical detector elements and two adjacent detector elements have an equal inclination angle, as shown in the left part of FIG. 4, the four detector elements are divided into three detector segments 1, 2, and 3. Similarly, the offset angle β corresponding to the right half of the detector segments 1, 2, and 3 have three different value ranges due to the different detector elements, namely, β range 1, β range 2, and β range 3, wherein:

(1) for β range 1, $$0 \leq \beta \leq \operatorname{atan}\left(\frac{\frac{L}{2}}{H}\right);$$

(2) for β range 2, and $$\operatorname{atan}\left(\frac{\frac{L}{2}}{H}\right) < \beta \leq \operatorname{atan}\left(\frac{\frac{L}{2} + \cos(\alpha) \times L}{H - \sin(\alpha) \times L}\right);$$

(3) for β range 3, $$\operatorname{atan}\left(\frac{\frac{L}{2} + \cos(\alpha) \times L}{H - \sin(\alpha) \times L}\right) < \beta \leq \left(\frac{\frac{L}{2} + \cos(\alpha) \times L + \cos(2\alpha) \times L}{H - \sin(\alpha) \times L - \sin(2\alpha) \times L}\right).$$

After the value ranges of the offset angle β have been determined, the distance H' from the focus of the X-ray tube to the X-ray detector through the various points on the OX axis may be determined according to the following equations:

$$H' = \frac{H}{\cos(\beta)}, \text{ wherein } 0 \leq \beta \leq \operatorname{atan}\left(\frac{\frac{L}{2}}{H}\right); \quad (1)$$

$$H' = \frac{H + \frac{L \times \tan(\alpha)}{2}}{\tan(\alpha) \times \sin(\beta) + \cos(\beta)}, \quad (2)$$

wherein $\operatorname{atan}\left(\frac{\frac{L}{2}}{H}\right) < \beta \leq \operatorname{atan}\left(\frac{\frac{L}{2} + \cos(\alpha) \times L}{H - \sin(\alpha) \times L}\right)$; and $$H' = \frac{H - L \times \sin(\alpha) + \frac{L \times \tan(2\alpha)}{2} + L \times \cos(\alpha) \times \tan(2\alpha)}{\tan(2\alpha) \times \sin(\beta) + \cos(\beta)}, \quad (3)$$

wherein $$\operatorname{atan}\left(\frac{\frac{L}{2} + \cos(\alpha) \times L}{H - \sin(\alpha) \times L}\right) < \beta \leq \operatorname{atan}\left(\frac{\frac{L}{2} + \cos(\alpha) \times L + \cos(2\alpha) \times L}{H - \sin(\alpha) \times L - \sin(2\alpha) \times L}\right).$$

Since the offset angle β corresponding to the left part of the detector segments 1 and 2 is symmetrical to the offset angle β corresponding to the right part of the detector segments 1 and 2, relative to the two-dimensional plane symmetry YOZ, the value ranges for the offset angle β corresponding to the left part of the detector segments 1 and 2 and the corresponding H' can be determined in a similar manner.

Thereafter, the profile of the two longitudinal opposite edges of the collimator slit can be determined according to the following equation based on the offset angle β and H':

$$\begin{cases} X(\beta) = \pm \tan(\beta) \times h \\ P(\beta) = \pm \dfrac{h \times D}{2H' \times \cos(\beta)} \end{cases}.$$

For the case where the X-ray detector comprises six identical detector elements and two adjacent detector elements have an equal inclination angle, as shown in the left part of FIG. 3, the six detector elements are divided into four detector segments 1, 2, 3 and 4. Similarly, the offset angle β corresponding to the right half of the detector segments 1, 2, 3 and 4 have four different value ranges due to the different detector elements, namely, β range 1, β range 2, β range 3, and β range 4, wherein:

(1) for β range 1, $$0 \leq \beta \leq \operatorname{atan}\left(\frac{\frac{L}{2}}{H}\right);$$

(2) for β range 2, $$\operatorname{atan}\left(\frac{\frac{L}{2}}{H}\right) < \beta \leq \operatorname{atan}\left(\frac{\frac{L}{2} + \cos(\alpha) \times L}{H - \sin(\alpha) \times L}\right);$$

(3) for β range 3, $$\operatorname{atan}\left(\frac{\frac{L}{2} + \cos(\alpha) \times L}{H - \sin(\alpha) \times L}\right) < \beta \leq \operatorname{atan}\left(\frac{\frac{L}{2} + \cos(\alpha) \times L + \cos(2\alpha) \times L}{H - \sin(\alpha) \times L - \sin(2\alpha) \times L}\right);$$

and (4) for β range 4, $$\operatorname{atan}\left(\frac{\frac{L}{2} + \cos(\alpha) \times L + \cos(2\alpha) \times L}{H - \sin(\alpha) \times L - \sin(2\alpha) \times L}\right) < \beta \leq$$

$$\operatorname{atan}\left(\frac{\frac{L}{2} + \cos(\alpha) \times L + \cos(2\alpha) \times L + \cos(3\alpha) \times L}{H - \sin(\alpha) \times L - \sin(2\alpha) \times L - \sin(3\alpha) \times L}\right).$$

After the value ranges of the offset angle β have been determined, the distance H' from the focus of the X-ray tube to the X-ray detector through the various points on the OX axis may be determined according to the following equations:

$$H' = \frac{H}{\cos(\beta)}, \text{ wherein } 0 \leq \beta \leq \operatorname{atan}\left(\frac{\frac{L}{2}}{H}\right); \quad (1)$$

$$H' = \frac{H + \frac{L \times \tan(\alpha)}{2}}{\tan(\alpha) \times \sin(\beta) + \cos(\beta)}, \quad (2)$$

wherein $\operatorname{atan}\left(\frac{\frac{L}{2}}{H}\right) < \beta \leq \operatorname{atan}\left(\frac{\frac{L}{2} + \cos(\alpha) \times L}{H - \sin(\alpha) \times L}\right);$ $$H' = \frac{H - L \times \sin(\alpha) + \frac{L \times \tan(2\alpha)}{2} + L \times \cos(\alpha) \times \tan(2\alpha)}{\tan(2\alpha) \times \sin(\beta) + \cos(\beta)}, \quad (3)$$

wherein $$\operatorname{atan}\left(\frac{\frac{L}{2} + \cos(\alpha) \times L}{H - \sin(\alpha) \times L}\right) < \beta \leq$$

$$\operatorname{atan}\left(\frac{\frac{L}{2} + \cos(\alpha) \times L + \cos(2\alpha) \times L}{H - \sin(\alpha) \times L - \sin(2\alpha) \times L}\right); \text{ and}$$

-continued $$H' = \frac{H - L \times \sin(\alpha) - L \times \sin(2\alpha) + \dfrac{L \times \tan(3\alpha)}{2} + L \times \cos(\alpha) \times \tan(3\alpha) + L \times \cos(2\alpha) \times \tan(3\alpha)}{\tan(3\alpha) \times \sin(\beta) + \cos(\beta)}, \quad (4)$$

wherein $$\operatorname{atan}\left(\frac{\dfrac{L}{2} + \cos(\alpha) \times L + \cos(2\alpha) \times L}{H - \sin(\alpha) \times L - \sin(2\alpha) \times L}\right) < \beta \leq$$

$$\operatorname{atan}\left(\frac{\dfrac{L}{2} + \cos(\alpha) \times L + \cos(2\alpha) \times L + \cos(3\alpha) \times L}{H - \sin(\alpha) \times L - \sin(2\alpha) \times L - \sin(3\alpha) \times L}\right).$$

Since the offset angle β corresponding to the left part of the detector segments 1, 2 and 3 is symmetric to the offset angle β corresponding to the right part of the detector segments 1, 2 and 3, relative to the two-dimensional plane symmetry YOZ, the value ranges for the offset angle β corresponding to the left part of the detector segments 1, 2 and 3 and the corresponding H' can be determined in a similar manner.

Thereafter, the profile of the two longitudinal opposite edges of the collimator slit can be determined according to the following equation based on the offset angle β and H':

$$\begin{cases} X(\beta) = \pm \tan(\beta) \times h \\ P(\beta) = \pm \dfrac{h \times D}{2H' \times \cos(\beta)} \end{cases}.$$

By determining the collimator slit profile according to the method 2300, the actual distribution of projection of the X-ray beam projected onto the X-ray detector after passing through such a collimator will be completely equal to the ideal, rectangular distribution of projection when there is no apparatus installation deviation. Besides, even if an apparatus installation deviation exists, there will just be a small amount of short-shoot and over-shoot areas at the two ends of the X-ray detector, as shown in FIG. 22. FIG. 22 shows the circumstance where the X-ray detector includes seven detector elements and where installation deviation exists.

Although the present invention has been described with reference to specific embodiments, it shall be understood that the present invention is not limited to these specific embodiments. Individuals skilled in the art will appreciate that various modifications, substitutions, changes and so on may be made to the present invention. For example, in the above embodiments one step or component may be divided into multiple steps or components; or, on the contrary, a plurality of steps or components in the above embodiments may be realized in one step or one component. All such variations should be considered within the scope of protection as long as they do not depart from the spirit of the present invention. In addition, the terms as used in the present specification and claims are not limitative, but descriptive. Moreover, according to actual needs, the entire or part of the features described in one specific embodiment can be incorporated into another embodiment.

What is claimed is:
1. A radiation CT imaging system, comprising:
   a radiation source arranged on a first side of a scan gantry the radiation source configured to emit radiation rays to the subject;
   a collimator disposed between the subject and the radiation source, the collimator configured to beamform the radiation rays from the radiation source, wherein the collimator comprises a planar gating device comprising at least one slit for passage of the radiation rays; and
   a radiation detector disposed on a second side of the scan gantry, the second side being opposite the first side, the radiation detector configured to detect the radiation rays transmitted;
   wherein the radiation detector comprises a plurality of detector elements arranged in a row, and there is an inclination angle between adjacent detector elements, and
   wherein a width distribution of each of the at least one slit in the longitudinal direction of the collimator is determined jointly by the following: a vertical distance between a focus of the radiation source and the slit, a vertical distance between the focus and the radiation detector, the inclination angle between adjacent detector elements, a length of each detector element, a desired width of projection on the radiation detector formed by the radiation rays passing through the slit, and an offset angle of a connecting line from a point on a longitudinal center line of the slit to the focus relative to a plane passing the focus and perpendicular to the slit.

2. The radiation CT imaging system according to claim 1, wherein the plurality of detector elements comprises three to seven detector elements.

3. The radiation CT imaging system according to claim 1, wherein the radiation rays are X-rays.

4. The radiation CT imaging system according to claim 3, wherein the plurality of detector elements comprises three to seven detector elements.

5. The radiation CT imaging system according to claim 1, further comprising:
   a collimator controller configured to select one of said plurality of slits.

6. The radiation CT imaging system according to claim 1, wherein the plurality of detector elements have a same or a different length.

7. The radiation CT imaging system according to claim 1, wherein the inclination angles between adjacent detector elements is equal.

8. The radiation CT imaging system according to claim 1, wherein the inclination angle between selected pairs of adjacent detector elements is not equal.

9. A method for determining a slit profile of a CT collimator, wherein the CT collimator comprises a planar gating device comprising at least one slit to allow radiation rays from a radiation source to be used in cooperation with the CT collimator to pass through and projected onto a radiation detector to be used in cooperation with the CT collimator, wherein the radiation detector comprises a plurality of detector elements arranged in a row, and there is an inclination angle between two adjacent detector elements, the method comprising:
   determining for each slit of the at least one slit a profile of two opposite edges in a longitudinal direction of the selected slit based on the following: a vertical distance between a focus of the radiation source to the slit, a vertical distance between the focus and the radiation detector, the inclination angle between adjacent detector elements, a length of each detector element, a desired width of projection on the radiation detector by the radiation rays passing through the slit, and an offset angle of a connecting line from a point on a longitudinal center line of the slit to the focus relative to a plane passing the focus and perpendicular to the slit.

10. The method according to claim 9, wherein the plurality of detector elements comprises three to seven detector elements.

11. The method according to claim 9, wherein the radiation rays are X-rays.

12. The method according to claim 9, wherein the plurality of detector elements have a same or a different length.

13. The method according to claim 9, wherein the inclination angles between adjacent detector elements is equal.

14. The method according to claim 9, wherein the inclination angle between selected pairs of adjacent detector elements is not equal.

* * * * *